United States Patent [19]

Teraji et al.

[11] Patent Number: 4,616,014

[45] Date of Patent: Oct. 7, 1986

[54] TRIAZINE DERIVATIVES, AND PHARMACEUTICAL COMPOSITIONS COMPRISING THE SAME

[75] Inventors: Tsutomu Teraji, Osaka; Youichi Shiokawa, Ibaraki; Kazuo Okumura, Sakai; Yoshinari Sato, Takaishi, all of Japan

[73] Assignee: Fujisawa Pharmaceutical Co., Ltd., Osaka, Japan

[21] Appl. No.: 433,513

[22] Filed: Oct. 8, 1982

[30] Foreign Application Priority Data

Oct. 22, 1981 [GB] United Kingdom ............... 8131900
Aug. 23, 1982 [GB] United Kingdom ............... 8224151

[51] Int. Cl.$^4$ ............... C07D 253/06; C07D 401/04; C07D 403/04; A61K 31/53
[52] U.S. Cl. ............... 514/242; 544/182; 540/523; 540/593
[58] Field of Search ............... 544/182, 112; 424/249, 424/248.5, 248.54, 248.57; 260/243.3; 542/449; 514/242

[56] References Cited

U.S. PATENT DOCUMENTS

| | | | |
|---|---|---|---|
| 4,157,392 | 6/1979 | Gullo et al. | 544/182 |
| 4,423,045 | 12/1983 | Brown et al. | 544/8 |
| 4,495,185 | 1/1985 | Brown et al. | 544/182 |
| 4,503,054 | 3/1985 | Brown et al. | 544/182 |
| 4,581,356 | 4/1986 | Teraji et al. | 544/182 |

FOREIGN PATENT DOCUMENTS 52442 5/1982 European Pat. Off. .
2391202 12/1978 France .

OTHER PUBLICATIONS

Jochins et al., Chemische Berichte, vol. 109, pp. 154-167 (1976).

Vinot et al., C. R. Acad. Sc. Paris, t. 270, pp. 1042-1044 (1970).
Mustafa et al., Chemical Abstracts, vol. 76, p. 34221g (1972).
Nakayama et al., Journal of Heterocyclic Chemistry, vol. 18, pp. 631-632 (1981).

*Primary Examiner*—John M. Ford
*Attorney, Agent, or Firm*—Oblon, Fisher, Spivak, McClelland & Maier

[57] ABSTRACT

New triazine derivatives represented by the formula:

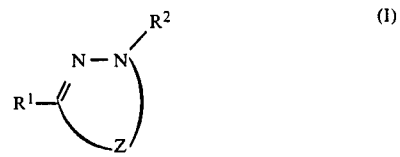

wherein $R^1$ is aryl, pyridyl, thienyl, 1,2,3,4-tetrahydroquinolyl or 1,3,4,5-tetrahydro-2H-1-benzazepinyl, optionally substituted with lower alkyl, lower alkoxy, halogen, nitro or oxo, $R^2$ is hydrogen, lower alkyl or carbamoyl substituted with lower alkyl or ar(lower)alkyl, and Z is a group selected from

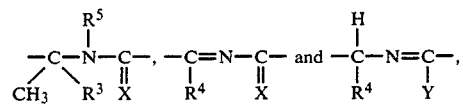

and pharmaceutically acceptable salt thereof, processes for preparation thereof and pharmaceutical compositions comprising the same of antihypertensive and antithrombotic activity.

18 Claims, No Drawings

TRIAZINE DERIVATIVES, AND PHARMACEUTICAL COMPOSITIONS COMPRISING THE SAME

The present invention relates to novel triazine derivatives and pharmaceutically acceptable salt thereof. More particularly, it relates to novel, partially hydrogenated triazine derivatives and pharmaceutically acceptable salts thereof which have antihypertensive activity and inhibitory activity on platelet aggregation, to processes for preparation thereof, to pharmaceutical composition comprising the same, and to a method of using the same therapeutically in the treatment of hypertension and thrombosis in human being and animals.

Accordingly, one object of this invention is to provide novel, partially hydrogenated triazine derivatives and pharmaceutically acceptable salts thereof, which are useful as an antihypertensive agent and antithrombotic agent.

Another object of this invention is to provide processes for preparation of said triazine derivatives and pharmaceutically acceptable salts thereof.

A further object of this invention is to provide pharmaceutical composition comprising, as an active ingredient, said triazine derivative or its pharmaceutically acceptable salt.

Still further object of this invention is to provide a method of using said triazine derivative or its pharmaceutically acceptable salt in the treatment of hypertension and thrombosis in human being and animals.

The object compounds of the present invention can be represented by the following formula [I].

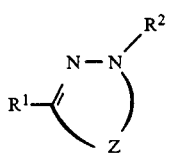

wherein
$R^1$ is aryl, pyridyl, thienyl, 1,2,3,4-tetrahydroquinolyl or 1,3,4,5-tetrahydro-2H-1-benzazepinyl, optionally substituted with lower alkyl, lower alkoxy, halogen, nitro or oxo;
$R^2$ is hydrogen, lower alkyl or carbamoyl substituted with lower alkyl or ar(lower)alkyl; and
Z is a group selected from

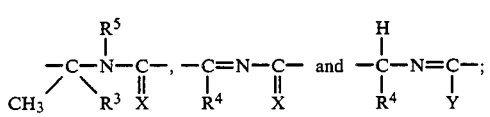

in which $R^3$ is hydrogen, lower alkyl or ar(lower)alkyl,
$R^4$ is lower alkyl,
$R^5$ is hydrogen, lower alkyl or carbamoyl substituted with lower alkyl or ar(lower)alkyl,
Y is O or S, and
Y is amino or hydrazino optionally substituted with cyano, halo-aryl, lower alkyl, lower alkylidene, hydroxy(lower)alkyl, lower alkylamino(lower)alkyl, pyrrolidinylmethylphenoxypropyl, formyloxy(lower)alkyl, amidino, methylamidino, 1-methylthio-1-(methylamino)methylene, cyanobenzylidene, acyl or N-containing heterocyclic group, wherein two lower alkyl and/or lower alkylidene groups on amino or hydrazino group can take together with nitrogen atom to form a N-containing heterocyclic group; or lower alkylthio optionally substituted with acyl.

The object compounds [I] as defined above can be more particularly represented by the following formulae.

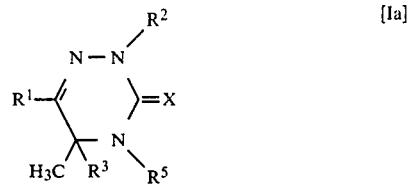

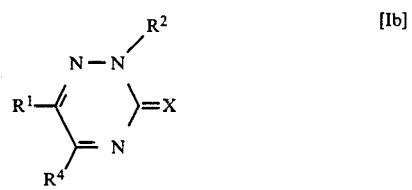

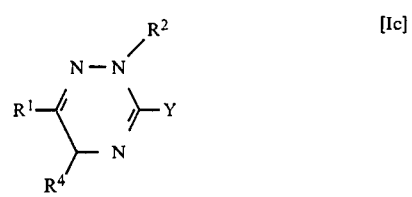

wherein $R^1$, $R^2$, $R^3$, $R^4$, $R^5$, X and Y are each as defined above.

With regard to the object compound [I], it should be understood that the compounds [I] include all of the possible optical and/or geometrical isomers due to the asymmetric carbon atoms and/or double bond in their molecule.

Suitable illustrations and examples of the above definitions are explained in the following.

The term "lower" is intended to mean a group having 1 to 6 carbon atoms, unless otherwise indicated.

Suitable "aryl" may be phenyl, tolyl, xylyl, naphthyl and the like, preferably phenyl or tolyl.

Suitable "1,2,3,4-tetrahydroquinolyl or 1,3,4,5-tetrahydro-2H-1-benzazepinyl optionally substituted with lower alkyl, lower alkoxy, halogen, nitro or oxo" may include 2-oxo-1,2,3,4-tetrahydroquinolyl, 3-oxo-1,2,3,4-tetrahydroquinolyl, 4-oxo-1,2,3,4-tetrahydroquinolyl, 1-methyl-2-oxo-1,2,3,4-tetrahydroquinolyl, 5-methoxy-2-oxo-1,2,3,4-tetrahydroquinolyl, 1-butyl-2-oxo-1,2,3,4-tetrahydroquinolyl, 6-chloro-2-oxo-1,2,3,4-tetrahydroquinolyl, 1,3,4,5-tetrahydro-2H-1-benzazepinyl, 2-oxo-1,3,4,5-tetrahydro-2H-1-benzazepinyl, 1-methyl-2-oxo-1,3,4,5-tetrahydro-2H-1-benzazepinyl, 1-methyl-6-chloro-2-oxo-1,3,4,5-tetrahydro-2H-1-benzazepinyl, 1-butyl-2-oxo-1,3,4,5-tetrahydro-2H-1-benzazepinyl, 1-methyl-4-oxo-1,3,4,5-tetrahydro-2H-1-benzazepinyl and the like.

Suitable "lower alkyl" may be straight or branched lower alkyl such as methyl, ethyl, propyl, isopropyl, butyl, isobutyl, sec-butyl, tert-butyl, pentyl, hexyl and the like, and preferably the one having 1 to 4 carbon atoms.

Suitable "lower alkoxy" may be methoxy, ethoxy, propoxy, isopropoxy, butoxy, sec-butoxy, tert-butoxy, isobutoxy, pentyloxy, hexyloxy and the like, and more preferably methoxy or ethoxy.

Suitable "halogen" may be chlorine, bromine, iodine or fluorine.

Suitable "carbamoyl substituted with lower alkyl or ar(lower)alkyl" may include lower alkyl carbamoyl (e.g. methylcarbamoyl, ethylcarbamoyl, propylcarbamoyl, isopropylcarbamoyl, butylcarbamoyl, pentylcarbamoyl, hexylcarbamoyl, etc.), and ar(lower)alkyl carbamoyl (e.g. benzylcarbamoyl α-methylbenzylcarbamoyl, α-ethylbenzylcarbamoyl, phenethylcarbamoyl, tolylmethylcarbamoyl, anisylcarbamoyl, etc.).

Suitable "ar(lower)alkyl" may be benzyl, phenethyl, tolylmethyl, xylylmethyl, naphthylmethyl, benzhydryl, α-methylbenzyl, phenylpropyl, anisyl, and the like, in which the most preferred one is benzyl.

Suitable "halo-aryl" may be aryl as mentioned before substituted with one or more halogen atom(s) such as fluorine, chlorine, bromine and iodine.

Suitable "lower alkylidene" may be methylene, ethylidene, propylidene, isopropylidene, butylidene, isobutylidene, 3-methylbutylidene, pentylidene, hexylidene and the like, and more preferably the one having 1 to 3 carbon atom(s).

Suitable "hydroxy(lower)alkyl" may be 1-hydroxyethyl, 2-hydroxyethyl, 1-hydroxypropyl, 2-hydroxypropyl, 3-hydroxypropyl, 1-hydroxyisopropyl, 2-hydroxyisopropyl, 1-hydroxybutyl, 2-hydroxybutyl, 3-hydroxybutyl, 4-hydroxybutyl, 1-hydroxyisobutyl, 2-hydroxyisobutyl, 3-hydroxyisobutyl, 5-hydroxypentyl, 6-hydroxyhexyl and the like, and more preferably the one having 1 to 3 carbon atom(s).

Suitable "lower alkylamino(lower)alkyl" may be mono- or di-lower alkylamino(lower)alkyl, such as methylaminomethyl, 1-methylaminoethyl, 2-methylaminoethyl, 3-methylaminopropyl, 4-methylaminobutyl, 6-methylaminohexyl, ethylaminomethyl, 2-ethylaminoethyl, 3-ethylaminopropyl, 4-ethylaminobutyl, 5-ethylaminopentyl, 6-ethylaminohexyl, propylaminomethyl, 2-propylaminoethyl, 3-propylaminopropyl, 4-propylaminobutyl, 6-propylaminohexyl, isopropylaminomethyl, 2-isopropylaminoethyl, 3-isopropylaminopropyl, 4-isopropylaminobutyl, N,N-dimethylaminomethyl, 2-N,N-dimethylaminoethyl, 3-N,N-dimethylaminopropyl, 3-N,N-dimethylaminobutyl, N,N-dimethylaminopentyl, N,N-dimethylaminohexyl, N,N-diethylaminomethyl, N,N-diethylaminoethyl, N,N-diethylaminopropyl, N,N-diethylaminobutyl, N,N-diethylaminopentyl, N,N-diethylaminohexyl and the like.

Suitable "pyrrolidinylmethylphenoxypropyl" may include 3-[3-(1-pyrrolidinylmethyl)phenoxy]propyl and the like.

Suitable "formyloxy(lower)alkyl" may include formyloxymethyl, formyloxyethyl and the like.

Suitable cyanobenzylidene" may include 4-cyanobenzylidene and the like.

Suitable "acyl"L9 may be a residue of a carboxylic acid or sulfonic acid and preferably lower alkanoyl (e.g., formyl, acetyl, propionyl, butyryl, isobutyryl, valeryl, isovaleryl, pivaloyl, etc.), and more preferably the one having 1 to 5 carbon atom(s); carbamoyl; lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.); lower alkanesulfonyl (e.g. mesyl, ethanesulfonyl, propanesulfonyl, isopropanesulfonyl, butansulfonyl, etc.); arenesulfonyl (e.g., benzenesulfonyl, tosyl, etc.); aroyl (e.g., benzoyl, toluoyl, naphthoyl, phthaloyl, etc.); ar(lower)alkanoyl (e.g., phenylacetyl, phenylpropionyl, etc.); ar(lower)alkoxycarbonyl (e.g., benzyloxycarbonyl, phenethyloxycarbonyl, etc.); heterocyclic carbonyl (e.g., thenoyl, furoyl, nicotinoyl, isonicotinoyl, etc.); and the like.

The acyl group as stated above may have 1 to 3 suitable substituent(s) such as halogen (e.g., chlorine, bromine, iodine or fluorine), hydroxy, amino, cyano, nitro, lower alkoxy (e.g. methoxy, ethoxy, propoxy, isopropoxy, etc.), lower alkyl (e.g., methyl, ethyl, propyl, isopropyl, butyl, etc.), lower alkenyl (e.g., vinyl, allyl, etc.), aryl (e.g., phenyl, tolyl, etc.), lower alkoxycarbonyl (e.g., methoxycarbonyl, ethoxycarbonyl, propoxycarbonyl, etc.) and lower alkoxycarbonylamino (e.g. methoxycarbonylamino, ethoxycarbonylamino, propoxycarbonylamino, etc.).

Suitable "N-containing heterocyclic group", which is a substituent on the amino or hydrozino group for Y, or which is formed by taken together two lower alkyl and/or lower alkylidene groups on the amino or hydrazino group with a nitrogen atom in the amino or hydrazino group for Y may be saturated or unsaturated, 5- or 6-membered, N-containing heterocyclic group such as pyrrolyl, imidazolyl, pyrazolyl, triazolyl, tetrazolyl, pyridyl, piperidino, piperazinyl, morpholino, pyrrolidinyl, imidazolinyl, and the like. These N-containing heterocyclic group may be substituted with lower alkyl, amino, methylthio, hydroxy(lower)alkyl or acyl as exemplified before.

Suitable "lower alkylthio" may be methylthio, ethylthio, propylthio, isopropylthio, butylthio, isobutylthio, t-butylthio, pentylthio, hexylthio and the like, and preferably the one having 1 to 3 carbon atoms.

Suitable "lower alkylthio substituted with acyl" may be lower alkylthio substituted with acyl as defined above, and more preferable one is lower alkylthio subsituted with lower alkoxycarbonyl(lower)alkanoyl.

Suitable pharmaceutically acceptable salts of the object compound [I] are conventional non-toxic salts and may include an acid addition salt such as an inorganic acid addition salt (e.g., chloride, bromide, sulfate, phosphate, etc.), an organic acid addition salt (e.g., oxalate, maleate, lactate, tartarate, fumarate, methanesulfonate, benzenesulfonate, toluenesulfonate, etc.) or a salt with an amino acid (e.g., arginine aspartic acid, glutamic acid, etc.), a salt with a base such as alkali metal salt (e.g., sodium salt, potassium salt, etc.), and the like.

The object compounds [I] of the present invention can be prepared by the following processes.

Process 1

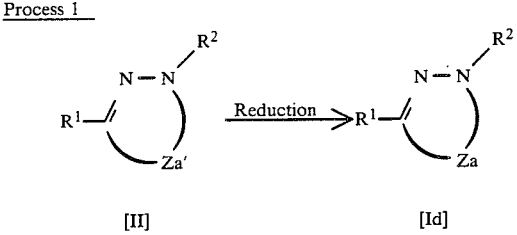

[II]  [Id]

Process 2

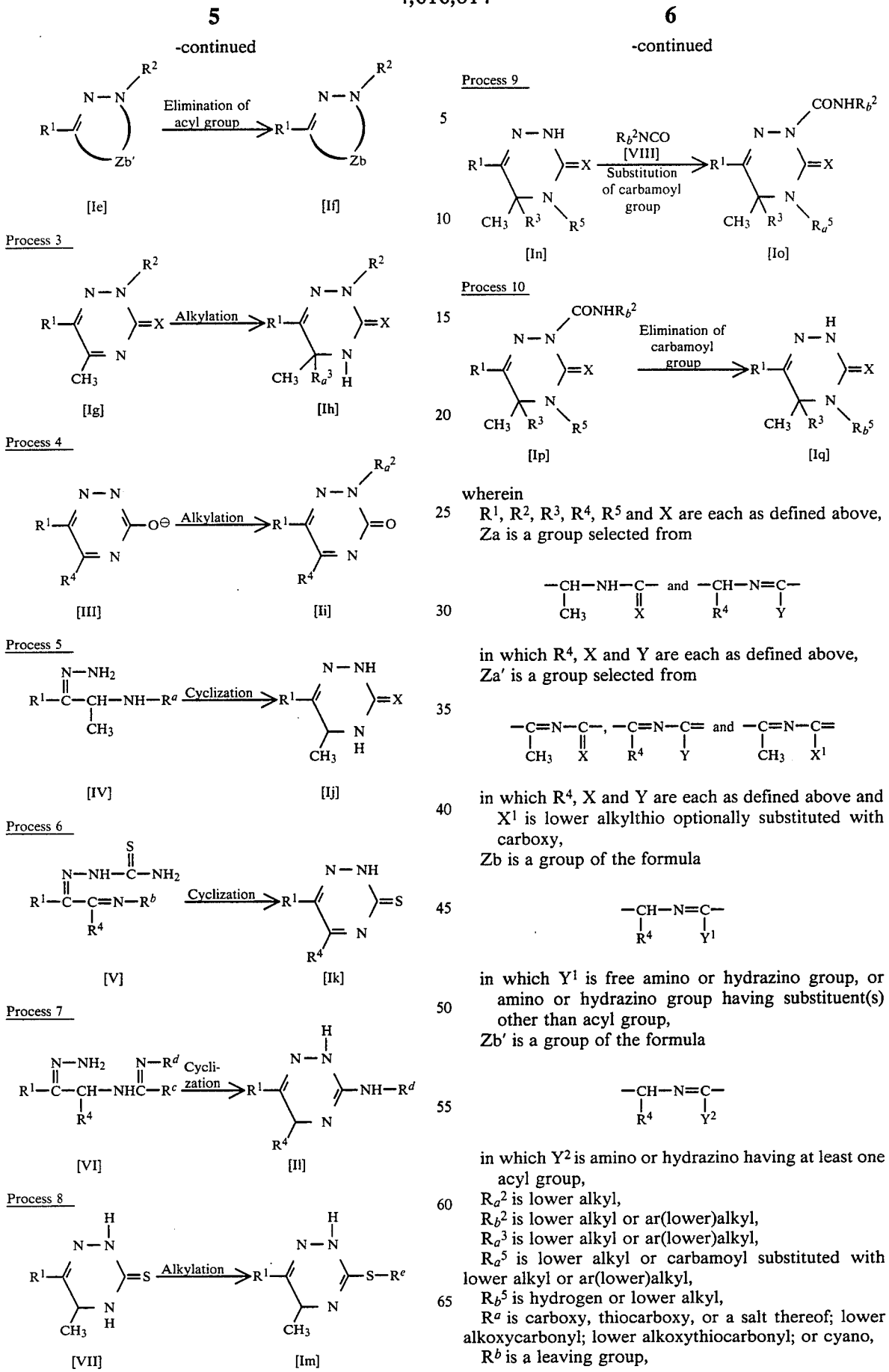

wherein
$R^1$, $R^2$, $R^3$, $R^4$, $R^5$ and X are each as defined above,
Za is a group selected from $$-\underset{\underset{CH_3}{|}}{CH}-NH-\underset{\underset{X}{\parallel}}{C}- \quad \text{and} \quad -\underset{\underset{R^4}{|}}{CH}-N=\underset{\underset{Y}{|}}{C}-$$

in which $R^4$, X and Y are each as defined above,
Za' is a group selected from $$-\underset{\underset{CH_3}{|}}{C}=N-\underset{\underset{X}{\parallel}}{C}-, \quad -\underset{\underset{R^4}{|}}{C}=N-\underset{\underset{Y}{|}}{C}= \quad \text{and} \quad -\underset{\underset{CH_3}{|}}{C}=N-\underset{\underset{X^1}{|}}{C}=$$

in which $R^4$, X and Y are each as defined above and $X^1$ is lower alkylthio optionally substituted with carboxy,
Zb is a group of the formula $$-\underset{\underset{R^4}{|}}{CH}-N=\underset{\underset{Y^1}{|}}{C}-$$

in which $Y^1$ is free amino or hydrazino group, or amino or hydrazino group having substituent(s) other than acyl group,
Zb' is a group of the formula $$-\underset{\underset{R^4}{|}}{CH}-N=\underset{\underset{Y^2}{|}}{C}-$$

in which $Y^2$ is amino or hydrazino having at least one acyl group,
$R_a^2$ is lower alkyl,
$R_b^2$ is lower alkyl or ar(lower)alkyl,
$R_a^3$ is lower alkyl or ar(lower)alkyl,
$R_a^5$ is lower alkyl or carbamoyl substituted with lower alkyl or ar(lower)alkyl,
$R_b^5$ is hydrogen or lower alkyl,
$R^a$ is carboxy, thiocarboxy, or a salt thereof; lower alkoxycarbonyl; lower alkoxythiocarbonyl; or cyano,
$R^b$ is a leaving group, $R^c$ is a leaving group, $R^d$ is an acyl or cyano group, and $R^e$ is lower alkyl optionally substituted with acyl.

Among the above definitions, suitable "lower alkylthio optionally substituted with carboxy" may be aforementioned lower alkylthio, carboxymethylthio, 2-carboxyethylthio, 3-carpboxypropylthio, 2-carboxypropylthio and the like.

Suitable "lower alkoxythiocarbonyl" may be methoxythiocarbonyl, ethoxythiocarbonyl, propoxythiocarbonyl and the like.

Suitable "leaving group" for $R^b$ may be hydroxy, lower alkoxy, and the like.

Suitable "leaving group" for $R^c$ may be hydroxy, lower alkoxy, lower alkylthio, and the like.

The aforementioned processes are explained in detail in the following.

Process 1

The compound [Id] and its salt can be prepared by reducing a compound [II] or its salt. The starting compound [II] includes both of known and new ones, and the new compound can be prepared according to the method described in the examples.

The reduction can be carried out by a conventional method, for example, by using a reducing agent such as lithium borohydride, sodium borohydride, potassium borohydride, sodium cyanoborohydride or lithium aluminium hydride etc.; by chemical reduction using metal (e.g., zinc, iron, copper, etc.) and acid (e.g., hydrochloric acid, sulfuric acid, etc.), or metal (e.g., sodium, lithium, zinc, etc.) and base (e.g., ammonia, sodium hydroxide, etc.) or by catalytic reduction. The catalytic reduction is usually carried out in the presence of a conventional catalyst, such as Raney nickel, palladium, platinum, rhodium, copper, etc. preferably at ambient temperature under atmospheric pressure and in a conventional solvent. The reduction using a reducing agent is usually carried out in a conventional solvent, preferably a polar solvent, such as water, tetrahydrofuran, methanol or ethanol, under cooling or at ambient temperature and optionally in the presence of a base, such as sodium hydroxide, sodium carbonate, potassium carbonate or sodium bicarbonate.

In the case that the partial structure of the starting compound [II] is

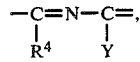

the double bond is hydrogenated by reduction to give a corresponding 4,5-dihydro-1,2,4-triazin-3(2H)-one (or thione) of the formula:

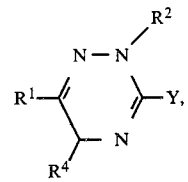

and in case that the partial structure of the starting compound [II] is

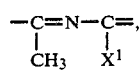

a double bond is hydrogenated by reduction to give a corresponding 2,5-dihydro-1,2,4-triazine compound of the formula:

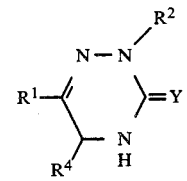

and further in case that the partial structure of the starting compound [II] is

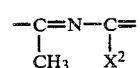

the reduction is usually conducted after treating a starting compound [II] with a base such as alkali metal hydroxide (e.g., sodium hydroxide, potassium hydroxide, etc.) to give a corresponding 4,5-dihydro-1,2,4-triazin-3(2H)-one of the formula:

$$R^1 \underset{R^4}{\overset{N-N\diagup R^2}{\diagdown}} = Y \atop N \atop H$$

In the course of this reaction, the corresponding olate compound having a partial structure $$-\underset{CH_3}{\overset{|}{C}}=N-\underset{X^2}{\overset{|}{C}}=$$

(in which $X^2$ is olate ion namely, $O^-$) is produced, and said compound can be optionally isolated and purified. This compound can be transformed to the ketone compound by treating with an acid (e.g. hydrochloric acid, sulfuric acid, etc.).

Process 2

The object compound [If] and its salt can be prepared by subjecting a compound [Ie] to the elimination reaction of the acyl group.

The elimination reaction is carried out in accordance with a conventional method such as hydrolysis or reduction. The hydrolysis may include a method using an acid, base or hydrazine and the like. These methods may be selected depending on the kind of the protective groups to be eliminated.

Among these methods, hydrolysis using an acid is one of the most common and preferable method for eliminating the acyl group such as lower alkoxycarbonyl (e.g., tertbutoxycarbonyl), lower alkanoyl (e.g., formyl, acetyl, etc.), cycloalkoxycarbonyl, aralkoxycarbonyl or the like. Suitable acid includes an organic or inorganic acid such as formic acid, trifluoroacetic acid, benzenesulfonic acid, p-toluenesulfonic acid, hydrochloric acid and the like.

When the elimination reaction is conducted with an acid, it can be carried out in a solvent such as water, a conventional organic solvent or a mixture thereof under cooling or at slightly elevated temperature.

Process 3

The object compound [Ih] and its salt can be prepared by reacting a compound [Ig] with an alkylating agent.

Suitable alkylating agent is an organic metal compound such as Grignard reagent or alkyl lithium (e.g., methyl lithium, butyl lithium etc.).

The Grignard reagent can be shown by the formula $R_a^3$-Mg-Hal (in which $R_a^3$ is as defined above, and Hal is halogen such as chlorine, bromine, iodine), and the reaction is carried out in a conventional solvent, preferably in an aprotic organic solvent such as dimethylether, diethylether, tetrahydrofuran etc., under cooling at room temperature or under warming.

Process 4

The object compound [Ii] can be prepared by reacting a compound [III] with an alkylating agent. The preferred alkylating agent may be lower alkyl halide such as lower alkyl chloride (e.g., propylchloride, butylchloride, etc.), lower alkyl bromide (e.g., methylbromide, ethylbromide, propylbromide, butylbromide, etc.), lower alkyl iodide (e.g., methyliodide, ethyliodide, propyliodide, etc.); lower alkylsulfate (e.g., dimethylsulfate, diethylsulfate, etc.), lower alkanesulfonate such as lower alkyl mesylate (e.g., methyl mesylate, ethyl mesylate, etc.) and lower alkyl tosylate (e.g., methyl tosylate, ethyl tosylate, etc.) and the like. The reaction can be conducted at ambient temperature or under heating, in a solvent such as alcohol (e.g. methanol, ethanol etc.) and water.

Process 5

The object compound [Ij] and its salt can be prepared by cyclization of a compound [IV].

The cyclization is usually carried out under warming or heating, in a solvent such as alcohol (e.g., methanol, ethanol, propanol, butanol, etc.). This reaction can be carried out in the presence or absence of hydrazine hydrate.

Process 6

The object compound [Ik] and its salt can be prepared by cyclization of a compound [V].

This reaction is preferably carried out in the presence of a base such as alkali metal carbonate (e.g., sodium carbonate, potassium carbonate, etc.), alkali metal bicarbonate (e.g. sodium bicarbonate, potassium bicarbonate, etc.), alkali metal hydroxide (e.g., sodium hydroxide, potassium hydroxide, etc.) or amine (e.g., trimethylamine, triethylamine, pyridine, etc.).

This reaction is usually carried out in a solvent such as water, alcohol (e.g., methanol, ethanol, propanol, butanol) or any other solvent which does not adversely influence the reaction. The reaction temperature is not critical, and the reaction is usually carried out under warming or heating.

Process 7

The object compound [Il] and its salt can be prepared by cyclization of a compound [VI].

The cyclization is carried out in a solvent such as alcohol (e.g., methanol, ethanol, propanol, butanol etc.), preferably in the presence of a base such as sodium alkoxide (e.g., sodium methoxide, etc.), secondary or tertiary amine (e.g., triethylamine, diethylamine, etc.) at room temperature or under warming.

Process 8

The object compound [Im] and its salt can be prepared by reacting a compound [VII] with an alkylating agent. The preferred alkylating agent may be a lower alkylhalide (e.g., lower alkylchloride, lower alkylbromide, lower alkyliodide), lower alkylsulfate (e.g., dimethylsulfate etc.), lower alkane sulfonate (e.g., lower alkyl mesylate, lower alkyl tosylate etc.) and the like. The reaction is usually carried out in a solvent such as alcohol (e.g., methanol, ethanol, propanol, etc.), at room temperature or under warming, and preferably in the presence of a base such as alkali metal hydroxide (e.g., sodium hydroxide, potassium hydroxide, etc.), alkali metal alkoxide (e.g., sodium methoxide, potassium methoxide, etc.), organic amine (e.g., triethylamine, ethylamine, etc.), Process 9

The object compound [Io] and its salt can be prepared by reacting a compound [In] or its salt with a compound [VIII].

The reaction is usually carried out in a inert solvent such as methylene chloride, tetrachloromethane, benzene, toluene, xylene and the like.

The reaction temperature is not critical, and the reaction can usually be conducted under cooling, at ambient temperature or under warming.

This reaction can preferably be conducted in a presence of a base such as organic amine (e.g. triethylamine, pyridine, etc.), inorganic base (e.g. sodium hydride, etc.), and the like.

Process 10

The object compound [Iq] and its salt can be prepared by subjecting a compound [Ip] to the elimination reaction of the carbamoyl group.

The elimination reaction is carried out in accordance with a conventional method such as hydrolysis. The hydrolysis can be conducted by using a base (e.g. dimethylamine, triethylamine, etc.) or an acid (e.g. p-toluenesulfonic acid, etc.), preferably under warming or heating in a solvent (e.g. xylene, toluene, etc.) or without a solvent.

The object compounds [I] obtained in the above Process 1 to 10 can be isolated and purified in a conventional manner, for example, extraction, precipitation, fractional chromatography, fractional crystallization, recrystallization, and the like.

The object compounds [I] thus prepared can be transformed into a pharmaceutically acceptable salt by a conventional method, if desired.

In case that the object compound [I] is a mixture of the optical isomers, optical resolution can optionally be conducted by conventional method.

The following antihypertensive test date and inhibitory activity test data on platelet aggregation shown that the compound [I] of the present invention exhibit a long lasting antihypertensive activity and inhibitory activity on platelet aggregation, and are useful as antihypertensive agents for treating hypertension and also as antithrombotic agents for treating thrombosis in animals and human being.

Test Method A

Five-week old male Wister rats were uninephrectomized under anesthesia. Deoxycorticosterone acetate (DOCA) (30 mg/kg), suspended in peanut oil, was injected subcutaneously twice a week and 1% saline was substituted for the drinking water. Animals with mean blood pressure 150–200 mmHg were used for experiment between 5 and 7 weeks after surgery.

The test compounds were administered intraperitoneally or orally. Blood pressure was measured at the femoral artery by means of a pressure transducer and recorded as electrically integrated values of mean arterial pressure.

Test Results A

Mean ratios of maximum decrease of blood pressure (mmHg) were shown in the following table.

| Test Compound (Example No.) | Dose | Effect Max (%) |
|---|---|---|
| 4-(2) | a | 48.9 |
| 6-(2) | a | 43.1 |
| 8-(2) | a | 48.9 |
| 10-(2) | a | 46.5 |
| 10-(2) | b | 50 |
| 25-(4) | a | 51.7 |
| 25-(4) | b | 37.4 |
| 32-(3), 37-(2) | a | 61.8 |
| 32-(3), 37-(2) | b | 58.3 |
| 36-(3) | a | 45.2 |
| 39-(2) | a | 57.1 |
| 39-(2) | b | 38.6 |
| 49-(3), 77-(2) | c | 43 |
| 49-(3), 77-(2) | d | 70 |
| 67-(3) | c | 43 |
| 68-(3) | d | 62 |
| 75 | c | 55 |
| 76 | d | 56 |

*a: The test compound were administered intraperitonealy in dose of 10 mg/kg.
*b: The test compound were administered orally in dose of 10 mg/kg.
*c: The test compound were administered orally in dose of 0.1 mg/kg.
*d: The test compound were administered orally in a dose of 1 mg/kg.

Furthermore, the above mentioned antihypertensive activity of these compounds were observed to continue more than 6 hours.

Test Method B

Platelet rich plasma (PRP) which contains $6.5-7.5 \times 10^8$ platelet/ml was prepared from rabbit blood. To the 200 μl of PRP, 5 μl of calcium chloride (1 mM) and 50 μl of pH 7.4 Tris-acetate solution (5 mM) containing 120 mM NaCl and test compound were added successively, and then stirred for 2 min. at 37° C. To the solution 5 μl of adenosine diphosphate (ADP) (2.5 μM) or collagen (2.5 μg/ml) was added as an aggregation inducer. Aggregation was measured by using an aggregometer (NKK HEMA TRACER 1). $ID_{50}$ was shown in Table 2.

Test Results B

| Test Compound | $ID_{50}$ (Mol) ADP | Collagen |
|---|---|---|
| Ex. 49-(3), 77-(2) | $1.6 \times 10^{-7}$ | $1.1 \times 10^{-7}$ |
| Ex. 67-(3) | $5.4 \times 10^{-8}$ | $1.8 \times 10^{-8}$ |
| Ex. 68-(3) | $1.4 \times 10^{-7}$ | $4.2 \times 10^{-8}$ |
| Ex. 71 | $9.8 \times 10^{-6}$ | $1.7 \times 10^{-5}$ |
| Ex. 75 | $9.8 \times 10^{-8}$ | $3.4 \times 10^{-8}$ |
| Ex. 76 | $1.2 \times 10^{-6}$ | $3.6 \times 10^{-7}$ |

As being apparent from the above test results, the object compounds [I] of the present invention are useful for antihypertensive medicines and antithrombotic medicines.

The effective ingredient may usually be administered with a does of 0.01 mg/kg to 500 mg/kg, 1 to 4 times a day in a preparations such as tablet, granule, powder, capsule, syrup, injection, suppository and the like. However, the above dosage may be increased or decreased according to the age, weight or conditions of the patient or the administering method.

The pharmaceutical preparation may be prepared in a conventional manner.

The following examples are given only for the purpose of illustrating the present invention in more detail.

EXAMPLE 1

(1) A mixture of 5-methyl-3-methylthio-6-phenyl-1,2,4-triazine (2.17 g) and N,N-diethylethylenediamine (2.99 g) was heated at 150° C. to 160° C. for 17 hours. The reaction mixture was dissolved in ethyl acetate, washed with water and brine, and then dried over sodium sulfate, which was treated with silical gel and filtered by suction. The filtrate was evaporated to dryness and the resulting residue was crystallized with diisopropyl ether under ice cooling. The resultant crystals were collected by filtration, washed with diisopropyl ether and dried to give 3-(2-diethylaminoethylamino)-5-methyl-6-phenyl-1,2,4-triazine (1.83 g).

NMR (CDCl$_3$, δ): 1.04 (6H, t, J=7 Hz), 2.41 (3H, s), 2.57 (4H, q, J=7 Hz), 2.70 (2H, t, J=5.8 Hz), 3.58 (2H, q, J=5.8 Hz), 5.91 (1H, b. s), 7.46 (5H, m)

(2) Sodium borohydride (2.13 g) was added portionwise to a stirred solution of the above obtained 3-(2-diethylaminoethylamino)-5-methyl-6-phenyl-1,2,4-triazine (3.14 g) in methanol (15 ml) at room temperature. The reaction mixture was filtered by suction, and the filtrate was concentrated under reduced pressure. The residue was subjected to column chromatography on silica gel (50 g) using a mixture of benzene and methylamine (40% in methanol) (100:1) as an eluent. The eluate was concentrated, and the residue was dissolved in benzene. The solution was extracted with 1N hydrochloride acid and then, made alkaline with an aqueous solution of sodium carbonate. The mixture was extracted with diethyl ether. The extract was washed with water, dried over sodium sulfate, and evaporated to give an oil of 3-(2-diethylaminoethylamino)-5-methyl-6-phenyl-2,5-dihydro-1,2,4-triazine (0.69 g).

NMR (CDCl$_3$, δ): 1.04 (6H, t, J=7.1 Hz), 1.25 (3H, d, J=5.8 Hz), 2.5~2.7 (2H, m), 2.55 (4H, q, J=7.1 Hz), 3.17~3.4 (2H, m), 4.68 (1H, q, J=5.8 Hz), 6.6 (1H, m), 7.25~7.5 (3H, m), 7.46~7.9 (2H, m)

Anal. Calcd. for C$_{16}$H$_{25}$N$_5$: C, 63.83; H, 8.88; H$_2$O N, 23.26; H$_2$O, 4.53. Found: C, 64.16; H, 8.75; N, 22.97; H$_2$O, 4.53.

EXAMPLE 2

(1) 3-[4-(2-Hydroxyethyl)-1-piperazinyl]-5-methyl-6-phenyl-1,2,4-triazine (2.11 g) was obtained by reacting 1-(2-hydroxyethyl)piperazine (2.8 g) with 5-methyl-3-methylthio-6-phenyl-1,2,4-triazine (2.17 g) in a similar manner to that of Example 1-(1). (crystallized from diethyl ether)

NMR (CDCl$_3$, δ): 2.45 (3H, s), 2.63 (6H, t, J=5.4 Hz), 3.70 (2H, t, J=5.4 Hz), 4.00 (4H, t, J=5.4 Hz), 7.47 (5H, m)

(2) Sodium borohydride (2.72 g) was added portionwise to a stirred solution of 3-[4-(2-hydroxyethyl)-1-piperazinyl]-5-methyl-6-phenyl-1,2,4-triazine (3.6 g) in methanol (15 ml) at room temperature. The reaction mixture was filtered by suction and the filtrate was evaporated. The resultant residue was extracted with ethyl acetate after addition of water, and the extract was washed with brine, dried over sodium sulfate and concentrated to a small volume. The resultant precipitates were collected by filtration, washed with diisopropyl ether and recrystallized from a mixture of ethyl acetate and diisopropyl ether to give 3-[4-(2-hydroxyethyl)-1-piperazinyl]-5-methyl-6-phenyl-2,5-dihydro-1,2,4-triazine (2.28 g), mp 103°~105° C.

NMR (CDCl$_3$, δ): 1.25 (3H, d, J=6.8 Hz), 2.45~2.75 (6H, m), 3.36 (4H, t, J=5 Hz), 3.68 (2H, t, J=5.3 Hz), 4.81 (1H, q, J=6.8 Hz), 7.35~7.62 (3H, m), 7.37~7.98 (2H, m)

Anal. Calcd. for C$_{16}$H$_{23}$N$_5$O: C, 63.76; H, 7.69; N, 23.24. Found: C, 63.67; H, 7.77; N, 22.96.

EXAMPLE 3

(1) A mixture of 5-methyl-3-methylthio-6-phenyl-1,2,4-triazine (4.15 g) and p-chloroaniline (4.22 g) was heated at 150° to 160° C. for 18 hours. After cooling, the resulting solid was washed successively with ethyl acetate, chloroform and methanol, and then dried to give 3-(4-chloroanilino)-5-methyl-6-phenyl-1,2,4-triazine (4.26 g).

NMR (DMSO-d$_6$, δ): 2.49 (3H, s), 7.39 (2H, d, J=9 Hz), 7.61 (5H, m), 7.93 (2H, d, J=9 Hz), 10.25 (1H, b, s)

(2) 3-(4-Chloroanilino)-5-methyl-6-phenyl-2,5-dihydro-1,2,4-triazine (3.60 g) was obtained by reacting sodium borohydride (4.3 g) with 3-(4-chloroanilino)-5-methyl-6-phenyl-1,2,4-triazine (4.25 g) in a similar manner to that of Example 2-(2).

mp 178.5°~180° C. (recrystallized from a mixture of ethanol and water)

NMR (DMSO-d$_6$, δ): 1.19 (3H, d, J=7 Hz), 4.70 (1H, q, J=7 Hz), 7.15~7.69 (7H, m), 7.69~7.93 (2H, m), 8.74 (2H, m)

EXAMPLE 4

(1) A mixture of 5-methyl-3-methylthio-6-phenyl-1,2,4-triazine (9 g) and N-(2-furoyl)piperazine (10 g) was heated at 150° to 160° C. for 89 hours with stirring. The reaction mixture was dissolved in benzene (300 ml) and subjected to chromatography on silica gel (300 g) using a mixture of benzene and ethyl acetate (3:2) as an eluent. The eluate was concentrated to dryness and the resulting solid was recrystallized from a mixture of chloroform and diisopropyl ether to give crystals of 3-[4-(2-furoyl)-1-piperazinyl]-5-methyl-6-phenyl-1,2,4-triazine (4.20 g), mp 141.5°~142.5° C.

NMR (CDCl$_3$, δ): 2.50 (3H, s), 4.05 (8H, s), 6.55 (1H, d, d, J=2, 3.5 Hz), 7.14 (1H, d, J=3.5 Hz), 7.57~7.78 (6H, m)

Anal. Calcd. for C$_{19}$H$_{19}$N$_5$O$_2$: C, 65.31; H, 5.48; N, 20.05. Found: C, 65.41; H, 5.43; N, 20.18.

(2) 3-[4-(2-Furoyl)-1-piperazinyl]-5-methyl-6-phenyl-2,5-dihydro-1,2,4-triazine was obtained by reacting sodium borohydride (3.81 g) with 3-[4-(2-furoyl)-1-piperazinyl]-5-methyl-6-phenyl-1,2,4-triazine (3.47 g) in a similar manner to that of Example 2-(2). The above obtained crude product was chromatographed on basic alumina (140 g) using a mixture of chloroform and methanol (20:1) as an eluent. The eluate was concentrated to a small volume and resulting precipitates were filtered off by suction. The filtrate was purified by column chromatography on silica gel (100 g) with methanol and then on neutral alumina with ethyl acetate as an eluent to give an oil of the object compound (2.2 g).

NMR (CDCL$_3$, δ): 1.24 (3H,d, J=6.7 Hz), 3.25~3.54 (4H, m), 3.67~4.0 (4H, m), 4.76 (1H, q, J=6.7 Hz), 6.48 (1H, d,d, J=1.8, 3.4 Hz), 7.04 (1H, d, J=3.4 Hz), 7.3~7.55 (4H, m), 7.65~7.9 (2H, m)

EXAMPLE 5

(1) 5-Methyl-3-(4-methyl-1-piperazinyl)-6-phenyl-1,2,4-triazine (3.9 g) was obtained by reacting N-methylpiperazine (8.17 g) with 5-methyl-3-methylthio-6-phenyl-1,2,4-triazine (5.37 g) in a similar manner to that of Example 1-(1).

NMR (CDCl$_3$, δ): 2.36 (3H, s), 2.45 (3H, s), 2.53 (4H, br. t, J=5 Hz), 4.01 (4H, br. t, J=5 Hz), 7.52 (5H, m)

(2) 5-Methyl-3-(4-methyl-1-piperazinyl)-6-phenyl-2,5-dihydro-1,2,4-triazine (1.31 g) was obtained by reacting sodium borohydride (2.43 g) and 5-methyl-3-(4-methyl-1-piperazinyl)-6-phenyl-1,2,4-triazine (4.12 g) in a similar manner to that of Example 2-(2). mp 124°~125° C. (crystallized from ethyl acetate)

NMR (CDCl$_3$, δ): 1.21 (3H, d, J=6.9 Hz), 2.27 (3H, s), 2.41 (4H, t, J=4.9 Hz), 3.33 (4H, t, J=4.9 Hz), 4.75 (1H, q, J=6.9 Hz), 7.25~7.53 (3H, m), 7.6~7.9 (2H, m), 8.26 (1H, m)

·Anal. Calcd. for C$_{15}$H$_{21}$N$_5$: C, 66.39; H, 7.80; N, 25.81. Found: C, 66.06; H, 7.79; N, 25.50.

EXAMPLE 6

(1) A mixture of 5-methyl-3-methylthio-6-phenyl-1,2,4-triazine (3 g) and ethanolamine (3 g) was heated at 150° to 160° C. for 5.25 hours. The reaction mixture was dissolved in ethyl acetate, washed with water and brine, dried over sodium sulfate and concentrated under reduced pressure. The residue was crystallized from a small amount of diethyl ether and then diisopropyl ether was added thereto. The crystals were collected by filtration, washed with diisopropyl ether and dried to give 3-(2-hydroxyethylamino)-5-methyl-6-phenyl-1,2,4-triazine (2.82 g).

NMR (CDCl$_3$, δ): 2.44 (3H, s), 3.5~4.05 (4H, m), 4.35 (1H, br. m), 7.49 (6H, m)

(2) 3-(2-Hydroxyethylamino)-5-methyl-6-phenyl-2,5-dihydro-1,2,4-triazine (1.40 g) was obtained by reacting sodium borohydride (1.8 g) with 3-(2-hydroxyethylamino)-5-methyl-6-phenyl-1,2,4-triazine (2.75 g) in a similar manner to that of Example 2-(2).

m.p. 138°~139° C. [recrystallized from ethanol and water (1:3)].

NMR (DMSO-d$_6$, δ): 1.04 (3H, d, J=7 Hz), 3.04~3.36 (2H, m), 3.38~3.70 (2H, m), 4.57 (1H, q, J=7 Hz), 5.6 (2H, m), 7.30~7.53 (3H, m), 7.64~7.85 (2H, m)

Anal. Calcd. for C$_{12}$H$_{16}$N$_4$O: C, 62.05; H, 6.94; N, 24.12. Found: C, 62.16; H, 6.89; N, 24.28.

EXAMPLE 7

(1)  3-N,N-Bis(2-hydroxyethyl)amino-5-methyl-6-phenyl-1,2,4-triazine (4.13 g) was obtained by reacting N,N-bis(2-hydroxyethyl)amine (6.63 g) with 5-methyl-3-methylthio-6-phenyl-1,2,4-triazine (6.8 g) in a similar manner so that of Example 1-(1). The purification was conducted with column chromatography on silica gel (85 g) using a mixture of benzene and ethyl acetate as an eluent.

NMR (CDCl$_3$,δ): 2.41 (3H, s), 3.93 (8H, s), 4.33 (2H, b.s.), 7.46 (5H, m)

(2)  3-[N,N-Bis(2-hydroxyethyl)amino]-5-methyl-6-phenyl-2,5-dihydro-1,2,4-triazine (0.85 g) was obtained by reacting sodium borohydride (2.78 g) with 3-[N,N-bis(2-hydroxyethyl)amino]-5-methyl-6-phenyl-1,2,4-triazine (4 g) in a similar manner to that of Example 2-(2). The purification was conducted with column chromatography on silica gel (50 g) using a mixture of ethyl acetate and methylamine (40% in methanol) (10:1), and then on neutral alumina (120 g) using a mixture of benzene, chloroform, and methanol (10:5:1) as an eluent.

NMR (CDCl$_3$, δ): 1.18 (3H, d, J=6.9 Hz), 2.97~3.9 (8H, m), 4.63 (1H, q, J=6.9 Hz), 6.83 (3H, s), 7.27~7.51 (3H, m), 7.61~7.85 (2H, m)

EXAMPLE 8

(1)  5-Methyl-3-morpholino-6-phenyl-1,2,4-triazine (2.40 g) was obtained by reacting N-aminomorpholine (3 g) with 5-methyl-3methylthio-6-phenyl-1,2,4-triazine (3.1 g) in a similar manner to that of Example 1-(1).

NMR (CDCl$_3$, δ): 2.46 (3H, s), 3.90 (8H, m), 7.54 (5H, m)

(2)  5-Methyl-3-morpholino-6-phenyl-1,2,4-triazine (2.32 g) was dissolved in ethanol (40 ml) containing anhydrous hydrogen chloride and hydrogenated over 10% palladium on carbon (0.33 g) under an atmospheric pressure at room temperature. After the theoretical amount of hydrogen gas was absorbed, the catalyst was filtered off, and the filtrate was evaporated under reduced pressure. The residual solid was recrystallized from ethanol to give crystals of 5-methyl-3-morpholino-6-phenyl-2,5-dihydro-1,2,4-triazine hydrochloride, mp 213°~215.5° C.

NMR (DMSO-d$_6$, δ): 1.27 (3H, d, J=6.9 Hz), 3.70 (8H, m), 4.92 (1H, q, J=6.9 Hz), 7.44~7.7 (3H, m), 7.8~8.03 (2H, m) 11.5 (2H, br. m)

Anal. Calcd. for C$_{14}$H$_{18}$N$_4$O.HCL: C, 57.04; H, 6.50; N, 19.01; Cl, 12.03. Found: C, 56.88; H, 6.55; N, 18.93; Cl, 12.15.

EXAMPLE 9

(1) A mixture of 5-methyl-3-methylthio-6-phenyl-1,2,4-triazine (20 g) and methylhydrazine (15.3 g) in ethanol (30 ml) was heated under reflux for 66 hours. After cooling, the reaction mixture was concentrated under reduced pressure and the residue was dissolved in chloroform. The solution was washed with water and brine successively, dried over sodium sulfate, and then evaporated. The residue was crystallized with diethyl ether, washed with diethyl ether, and dried to give 5-methyl-3-(1-methylhydrazino)-6-phenyl-1,2,4-triazine (13.91 g).

NMR (CDCl$_3$, δ): 2.47 (3H, s), 3.47 (3H, s), 4.59 (2H, b.s.), 7.50 (5H, m)

(2)  5-Methyl-3-(1-methylhydrazino)-6-phenyl-1,2,4-triazine (2.9 g) was dissolved in ethanol (50 ml) containing anhydrous hydrogen chloride and hydrogenated over 5% palladium on carbon (0.33 g) under atmospheric pressure at room temperature. After the theoretical amount of hydrogen gas was absorbed, the catalyst was filtered off, and the filtrate was concentrated under reduced pressure. The residue was neutralized with an aqueous solution of sodium carbonate and extracted with ethyl acetate. The extract was dried over sodium sulfate and concentrated under reduced pressure. The residual solid was recrystallized from ethanol to give colorless crystals of 5-methyl-3-(1-methylhydrazino)-6-phenyl-2,5-dihydro-1,2,4-triazine, mp 139.5°~141° C.

NMR (CDCL$_3$, δ): 1.23 (3H, d, J=6.8 Hz), 3.17 (3H, s), 3.64 (2H, br. m), 4.75 (1H, q, J=6.8 Hz), 7.28~7.53 (3H, m), 7.65~7.9 (2H, m), 9.0 (1H, br. m)

Anal. Calcd. for C$_{11}$H$_{15}$N$_5$: C, 60.81; H, 6.96; N, 32.23. Found: C, 60.96; H, 6.91; N, 32.36.

(3)  6N-Hydrochloric acid (1 drop) was added to a stirred solution of 5-methyl-3-(1-methylhydrazino)-6-phenyl-1,2,4-triazine (0.71 g) and 4-cyanobenzaldehyde (0.44 g) in methanol (5 ml) at room temperature and then the stirring was continued for 5 minutes. The mixture was evaporated under reduced pressure, the residue was triturated with diethyl ether, and the precipitates were collected by filtration to give 3-[2-(4-cyanobenzylidene)-1-methylhydrazino]-5-methyl-6phenyl-1,2,4-triazine (0.95 g).

NMR (DMSO-d$_6$, δ): 2.50 (3H, s), 3.76 (3H, s), 7.43~8.1 (9H, m), 8.12 (1H, s)

(4) 3-[2-(4-Cyanobenzylidene)-1-methylhydrazino]-5-methyl-6-phenyl-2,5-dihydro-1,2,4-triazine is obtained from the compound obtained in the above (3) in a similar manner to that of Example 1-(2).

EXAMPLE 10

(1)  5-Methyl-6-phenyl-3-piperidino-1,2,4-triazine (1.52 g) was obtained by reacting N-aminopiperidine (3 g) with 5-methyl-3-methylthio-6-phenyl-1,2,4-triazine (3 g) in a similar manner to that of Example 1-(1). The purification was conducted with column chromatography on silica gel (100 g) using a mixture of benzene and ethyl acetate (20:1) as an eluent.

NMR (CDCl$_3$, δ): 1.71 (6H, m), 2.43 (3H, s), 3.92 (4H, m), 7.47 (5H, m)

(2)  5-Methyl-6-phenyl-3-piperidino-2,5-dihydro-1,2,4-triazine (0.79 g) was obtained by reduction of the corresponding triazine compound (1.52 g) with 10% palladium on carbon (0.3 g) in a similar manner to that of Example 9-(2). mp 131°~132° C. (recrystallized from benzene).

NMR (CDCl$_3$, δ): 1.22 (3H, d, J=7 Hz), 1.59 (6H, m), 3.26 (4H, m), 4.69 (1H, q, J=7 Hz), 7.2~7.5 (3H, m), 7.6~7.85 (2H, m)

Anal. Calcd. for C$_{15}$H$_{20}$N$_4$: C, 70.28; H, 7.86; N, 21.86. Found: C, 70.34; H, 7.89; N, 21.97.

EXAMPLE 11

(1) m-Chloroperbenzoic acid (20 g) was added to a stirred solution of 5-methyl-3-methylthio-6-phenyl-1,2,4-triazine (20 g) in chloroform (600 ml) under ice cooling, and the mixture was stirred for 30 minutes at room temperature. The reaction mixture was washed with a saturated aqueous solution of sodium bicarbonate, dried over sodium sulfate, and then concentrated. The resulting residue was crystallized with diethyl ether, and the crystals were collected by filtration, washed with diethyl ether and dried to give 5-methyl-3-methylsulfinyl-6-phenyl-1,2,4-triazine (19.0 g).

NMR (CDCl$_3$, δ): 2.79 (3H, s), 3.13 (3H, s), 7.65 (5H, m)

(2) 5-Methyl-3-methylsulfonyl-6-phenyl-1,2,4-triazine (9.27 g) was obtained by reacting m-chloroperbenzoic acid (9.6 g) and 5-methyl-3-methylsulfinyl-6-phenyl-1,2,4-triazine (10 g) in a similar manner to that of Example 11-(1).

NMR (CDCl$_3$, δ): 2.77 (3H, s), 3.51 (3H, s), 7.64 (5H, m)

(3) n-Butyllithium (25 g/250 ml solution in hexane) (28.5 ml) was added dropwise to a stirred solution of N-aminopiperidine (4.12 g) in tetrahydrofurane (40 ml) at −78° C. and the stirring was continued for 2 hours at room temperature. A solution of 5-methyl-3-methylsulfonyl-6-phenyl-1,2,4-triazine (5 g) in tetrahydrofuran (100 ml) was added dropwise to the above obtained solution at −78° C. in 70 minutes with stirring and the stirring was continued for 30 minutes at the same temperature. The reaction mixture was washed with water and brine, and then extracted with ethyl acetate. The extract was washed with brine, dried over sodium sulfate and evaporated. The resulting residue was dissolved in chloroform and extracted with an aqueous solution of 6N-hydrochloric acid. The extract was made alkaline with an aqueous solution of potassium carbonate and extracted with ethyl acetate. The extract was washed with water, dried over sodium sulfate, and evaporated. Thus obtained crude product (3.82 g) was purified by chromatography on silica gel (100 g) using a mixture of benzene and ethyl acetate (2:1) as an eluent and recrystallized from diisopropyl ether to give crystals of 5-methyl-6-phenyl-3-piperidinoamino-1,2,4-triazine (2.25 g).

NMR (CDCl$_3$, δ): 1.34~2.06 (6H, m), 2.49 (3H, s), 2.94 (4H, br.t., J=5.1 Hz), 6.32 (1H, b.s.), 7.53 (5H, m)

(4) 5-Methyl-6-phenyl-3-piperidinoamino-1,2,4-triazine (2.25 g) was dissolved in ethanol (50 ml) containing anhydrous hydrogen chloride and hydrogenated over 5% palladium on carbon (0.38 g) under atmospheric pressure at room temperature. After the theoretical amount of hydrogen gas was absorbed, the catalyst was filtered off, and the filtrate was concentrated under reduced pressure. The residue was neutralized with an aqueous solution of sodium carbonate and extracted with ethyl acetate. The extract was dried over sodium sulfate, concentrated under reduced pressure and the residual solid was recrystallized from ethanol to give colorless crystals of 5-methyl-6-phenyl-3-piperidinoamino-2,5-dihydro-1,2,4-triazine (1.46 g), mp 188.5°~189.5° C.

NMR (CDCl$_3$, δ): 1.28 (3H, d, J=6.5 Hz), 1.40~1.94 (6H, m), 2.70 (4H, br.t, J=5 Hz), 4.66 (1H, q, J=6.5 Hz), 7.30~7.56 (3H, m), 7.57~7.90 (2H, m)

Anal. Calcd. for C$_{15}$H$_{21}$N$_5$: C, 66.39; H, 7.80; N, 25.81. Found: C, 66.59; H, 7.95; N, 25.99.

EXAMPLE 12

Sodium borohydride (3.4 g) was added portionwise to a stirred solution of 5-methyl-3-methylthio-6-phenyl-1,2,4-triazine (10 g) in tetrahydrofuran (25 ml). To the reaction mixture was added ethyl acetate, and the mixture was washed successively with 1N-hydrochloric acid, water and brine, dried over sodium sulfate, and concentrated to dryness. The residual solid was recrystallized from a mixture of ethanol and water to give 5-methyl-3-methylthio-6-phenyl-2,5-dihydro-1,2,4-triazine (3.46 g), m.p. 159°~160° C.

NMR (CDCl$_3$, δ): 1.27 (3H, d, J=7 Hz), 2.50 (3H, s), 4.92 (1H, q, J=7 Hz), 7.26~7.53 (3H, m), 7.64~7.84 (2H, m)

Anal. Calcd. for C$_{11}$H$_{13}$N$_3$S: C, 60.24; H, 5.97; N, 19.16. Found: C, 60.50; H, 6.00; N, 19.28.

EXAMPLE 13

(1) A solution of 5-methyl-3-methylthio-6-phenyl-1,2,4-triazine (7 g) and hydrazine hydrate (5 ml) in ethanol (15 ml) was heated under reflux for 8 hours. The reaction mixture was evaporated and the resultant residue was washed with water, dried and recrystallized from a mixture of ethanol and water (5:3) to give crystals of 3-hydrazino-5-methyl-6-phenyl-1,2,4-triazine (3.76 g), m.p. 136.5°~137.5° C.

NMR (DMSO-d$_6$, δ): 2.40 (3H, s), 4.44 (2H, s), 7.55 (5H, m), 8.65 (1H, s)

Anal. Calcd. for C$_{10}$H$_{11}$N$_5$: C, 59.69; H, 5.51; N, 34.80. Found: C, 59.38; H, 5.34; N, 34.63.

(2) A mixture of 3-hydrazino-5-hydrazino-5-methyl-6-phenyl-1,2,4-triazine (6.6 g), triethylamine (5.4 g), 2-t-butoxycarbonyloxyimino-2-phenylacetonitrile (9.76 g) in tetrahydrofuran (60 ml) was heated at 63° C. for 5.5 hours with stirring and then allowed to stand at room temperature for 61 hours. The mixture was treated with diisopropyl ether (40 ml), and the resultant precipitates were collected by filtration, washed successively with diisopropyl ether, methanol and diisopropyl ether, and dried to give 3-(2-t-butoxycarbonylhydrazino)-5-methyl-6-phenyl-1,2,4-triazine (8.92 g).

NMR (DMSO-d$_6$, δ): 1.48 (9H, s), 2.43 (3H, s), 7.56 (5H, m), 9.04 (1H, b.s.), 9.36 (1H, b.s.)

(3) 3-(2-t-Butoxycarbonylhydrazino)-5-methyl-6-phenyl-2,5-dihydro-1,2,4-triazine (8.09 g) was obtained by reduction of the corresponding triazine compound (8.92 g) in a similar manner to that of Example 2-(2). (recrystallized from methanol)

NMR (DMSO-d$_6$, δ): 1.17 (3H, d, J=6.7 Hz), 1.42 (9H, s), 4.54 (1H, q, J=6.7 Hz), 7.36 (3H, m), 7.67 (2H, m), 8.2 (3H, m)

(4) 3-(2-t-Butoxycarbonylhydrazino)-5-methyl-6-phenyl-2,5-dihydro-1,2,4-triazine (5.27 g) was dissolved in a saturated methanolic solution of hydrogen chloride (40 ml), and the solution was allowed to stand at room temperature for 3.5 hours. The reaction mixture was evaporated under reduced pressure and the residual solid was recrystallized from ethanol to give colorless crystals of 3-hydrazino-5-methyl-6-phenyl-2,5-dihydro-1,2,4-triazine hydrochloride (3.99 g), m.p. 214°~215° C.

NMR (DMSO-d$_6$, δ): 1.28 (3H, d, J=7.9 Hz), 4.6 (2H, m), 4.93 (1H, q, J=7.9 Hz), 7.4~7.67 (3H, m), 7.7~8.03 (2H, m), 9.6 (2H, m), 11.96 (1H, m)

Anal. Calcd. for C$_{10}$H$_{13}$N$_5$.HCL: C, 50.10; H, 5.89; Cl, 14.79; N, 29.22. Found: C, 49.98; H, 5.88; Cl, 14.48; N, 28.94.

EXAMPLE 14

(1) A solution of ethyl chloroformate (1.98 g) in methylene chloride (5 ml) was added dropwise to a stirred solution of 3-hydrazino-5-methyl-6-phenyl-1,2,4-triazine (3.68 g) in methylene chloride (40 ml) under ice cooling in 15 minutes, and the reaction mixture was treated with a solution of triethylamine (1.8 g) in methylene chloride (10 ml) under ice cooling. The reaction mixture was concentrated under reduced pressure. The residue was extracted with ethyl acetate after addition of water. The extract was washed with 5% hydrochloric acid and water, dried over magnesium sulfate, concentrated under reduced pressure, and the residue was pulverized with diisopropyl ether. The resulting precipitates were collected by filtration, washed with water and dried to give 3-(2-ethoxycarbonylhydrazino)-5-methyl-6-phenyl-1,2,4-triazine (3.23 g).

NMR (CDCl$_3$, δ): 1.30 (3H, t, J=7.1 Hz), 2.50 (3H, s), 4.26 (2H, q, J=7.1 Hz), 7.03 (1H, m), 7.54 85H, s)

(2) 3-(2-Ethoxycarbonylhydrazino)-5-methyl-6-phenyl-2,5-dihydro-1,2,4-triazine (1.02 g) was obtained by reacting sodium borohydride (0.47 g) with 3-(2-ethoxycarbonylhydrazino)-5-methyl-6-phenyl-1,2,4-triazine (1.93 g) in a similar manner to that of Example 2-(2). m.p. 186.5°~187° C. (decomp.)(recrystallized from ethanol)

NMR (DMSO-d$_6$, δ): 1.17 (3H, d, J=6.9 Hz), 1.18 (3H, t, J=7 Hz), 4.05 (2H, q, J=7 Hz), 4.55 (1H, q, J=6.9 Hz), 7.31~7.53 (3H, m), 7.61~7.85 (2H, m), 8.6 (2H, br.m)

Anal. Calcd. for C$_{13}$H$_{17}$N$_5$O$_2$: C, 56.71; H, 6.22; N, 25.44. Found: C, 56.98; H, 6.10; N, 25.95.

EXAMPLE 15

(1) Acetic anhydride (1.6 g) was added dropwise to a stirred solution of 3-hydrazino-5-methyl-6-phenyl-1,2,4-triazine (3 g) in methylene chloride (30 ml) under ice cooling and then the stirring was continued for 15 minutes. The solution was washed with water, dried over sodium sulfate and concentrated under reduced pressure. The residue was crystallized from a mixture of methylene chloride and diisopropyl ether to give 3-(2-acetylhydrazino)-5-methyl-6-phenyl-1,2,4-triazine (3.37 g).

NMR (CDCl$_3$, δ): 2.14 (3H, s), 2.48 (3H, s), 7.52 (5H, s), 7.94 (1H, b.s.), 9.20 (1H, b.s.)

(2) Sodium borohydride (1.11 g) was added to a stirred solution of 3-(2-acetylhydrazino)-5-methyl-6-phenyl-1,2,4-triazine (3.29 g) in methanol (30 ml) at room temperature and then the stirring was continued for 1 hour. The precipitates were collected by filtration, washed successively with water, methanol, and diisopropyl ether, and then recrystallized from a mixture of methanol and water to give colorless crystals of 3-(2-acetylhydrazino)-5-methyl-6-phenyl-2,5-dihydro-1,2,4-triazine (1.39 g), m.p. 204.5°~205° C. (decomp.).

NMR (DMSO-d$_6$, δ): 1.17 (3H, d, J=6.7 Hz), 1.84 (3H, s), 4.56 81H, q, J=6.7 Hz), 7.34~7.56 (3 H, m), 7.63~7.87 (2H, m)

Anal. Calcd. for C$_{12}$H$_{15}$N$_5$O: C, 58.76; H, 6.16; N, 28.55. Found: C, 58.50; H, 6.00; N, 28.10.

EXAMPLE 16

(1) Formic acid (5 ml) was added dropwise to acetic anhydride (10 ml) with stirring under ice cooling, and stirred at 50° C. for 15 minutes. To the solution was added 3-hydrazino-5-methyl-6 -phenyl-1,2,4-triazine (5g) with stirring under ice cooling, and the stirring was continued for 50 minutes under ice cooling. The reaction mixture was poured into ice water, and the resultant precipitates were collected by filtration and washed with water. The above obtained solid was dissolved in methanol (100 ml), the solution was treated with 28% ammonium hydroxide (14 drops) and evaporated to give white powder of 3-(2-formylhydrazino)-5-methyl-6-phenyl-1,2,4-triazine (4.505 g).

IR (Nujol): 3220, 1685 cm$^{-1}$

NMR (DMSO-d$_6$, δ): 2.42 (3H, s), 7.4~7.6 (5H, m), 8.18 (1H, s), 9.5 (1H, b.s.), 10.1 (1H, b.s.)

(2) A solution of 3-(2-formylhydrazino)-5-methyl-6-phenyl-1,2,4-triazine (2.71 g) in acetic acid (60 ml) was hydrogenated over 5% palladium on carbon (2 g) under atmospheric pressure at room temperature. After the theoretical amount of hydrogen gas was absorbed, the catalyst was filtered off, washed with methanol, and the filtrate was evaporated. The residue was dissolved in water, and the solution was washed with chloroform, neutralized with an aqueous solution of sodium carbonate, and extracted with chloroform. The extract was washed with water, dried over magnesium sulfate, and concentrated under reduced pressure. The resultant residue was recrystallized from methanol to give colorless crystals of 3-(2-formylhydrazino)-5-methyl-6-phenyl-2,5-dihydro-1,2,4-triazine (0.59 g), m.p. 216°~219° C. (decomp.).

NMR (DMSO-d$_6$, δ): 1.18 (3H, d, J=6.7 Hz), 3.33 (1H, br.m), 4.58 (1H, g, J=6.7 Hz), 7.35~7.6 (3H, m), 7.6~7.83 (2H, m), 7.87 (1H, s), 9.40 (2H, br.m)

Anal. Calcd. for C$_{11}$H$_{13}$N$_5$O: C, 57.13; H, 5.67; N, 30.29. Found: C, 57.13; H, 5.59; N, 30.08.

EXAMPLE 17

(1) A solution of ethyl chloroformate (1.628 g) in methylene chloride (6 ml) was added dropwise to a stirred solution of acetoxyacetic acid (1.77 g) and triethylamine (1.515 g) in methylene chloride (30 ml) under ice cooling in 3 minutes, and the stirring was continued for 10 minutes under ice cooling. To the mixture was added quickly a solution of 3-hydrazino-5-methyl-6-phenyl-1,2,4-triazine (2.01 g) in chloroform (28 ml) with stirring under ice cooling, and then the stirring was continued for 20 minutes. The solution was washed with water, dried over sodium sulfate, and concentrated. The resultant residue was dissolved in methanol (50 ml), and a solution of sodium hydroxide (0.8 g) in water (10 ml) was added thereto under ice cooling. After stirring for 0.5 hours, the solution was evaporated under reduced pressure and the residue was dissolved in water. To the solution was added dry ice and then the solution was concentrated under reduced pressure. The resultant precipitates were collected by filtration, washed with cold water and dried. On the other hand, the filtrate was salted out and extracted with ethyl acetate. The extract was dried over magnesium sulfate and evaporated to give a solid residue. The residue was combined with the substance obtained above, and recrystallized from a mixture of ethyl acetate and ethanol to give colorless crystals of 3-(2-hydroxyacetylhydrazino)-5-methyl-6-phenyl-1,2,4-triazine (1.852 g).

IR (Nujol): 3200, 3100 (shoulder), 3050 (shoulder), 1675 cm$^{-1}$

NMR (DMSO-d$_6$): 2.41 (3H, s), 4.04 (2H, d, J=6Hz), 5.53 (1H, t, J=6Hz), 7.4~7.7 (5H, m), 9.4 (1H, b.s.), 9.86 (1H, b.s.)

(2) Sodium borohydride (0.494 ) was added portionwise to a stirred solution of 3-(2-hydroxyacetylhydrazino)-5-methyl-6-phenyl-1,2,4-triazine (1.684 g) in methanol (30 ml) under ice cooling in 10 minutes and the stirring was continued for 1.5 hours at the same temperature. The reaction mixture was evaporated and the residue was dissolved in water. The solution was passed through a column of DIAION HP-20 (Trademark, manufactured by Mitsubishi Chemical Industries Ltd.) (80 ml) and eluted with water and then with methanol. The methanol eluate was evaporated under reduced pressure and the residual solid was recrystallized from methanol to give colorless crystals of 3-(2-hydroxyacetylhydrazino)-5-methyl-6-phenyl-2,5-dihydro-1,2,4-triazine (0.644 g), m.p. 167°~168° C. (decomp.)

IR (Nujol): 3200, 1640 cm$^{-1}$

NMR (DMSO-d$_6$, δ): 1.20 (3H, d, J=6.5 Hz), 3.92 (2H, s), 4.59 (1H, q, J=6.5 Hz), 7.3~7.6 (3H, m), 7.6~7.9 (2H, m)

Anal. Calcd. for C$_{12}$H$_{15}$N$_5$O$_2$: C, 55.16; H, 5.79; N, 26.81. Found: C, 55.02; H, 5.69; N, 26.87.

EXAMPLE 18

(1) A solution of n-valeryl chloride (1.93 g) in methylene chloride (3 ml) was added dropwise to a stirred solution of 3-hydrazino-5-methyl-6-phenyl-1,2,4-triazine (3.224 g) and triethylamine (1.784 g) in methylene chloride (40 ml) under ice cooling, and the stirring was continued for 30 minutes. The reaction mixture was evaporated and the resultant residue was extracted with ethyl acetate after addition of water. The extract was washed successively with 5% hydrochloric acid, water, a saturated aqueous solution of sodium bicarbonate and water, dried over magnesium sulfate, and then concentrated to a small volume under reduced pressure. The resultant residue was crystallized from diethyl ether, collected by filtration, washed with diethyl ether and dried to give 5-methyl-6-phenyl-3-(2-valerylhydrazino)-1,2,4-triazine (3.406 g).

IR (Nujol): 3250, 3200 (shoulder), 1650 cm$^{-1}$

NMR (DMSO-d$_6$, δ): 0.89 (3H, t, J=6 Hz), 1.5 (4H, broad m), 2.2 82H, t, J=6 Hz), 2.38 (3H, s), 7.35~7.73 (5H, m), 9.26 (1H, s), 9.78 (1H, s)

(2) 5-Methyl-6-phenyl-3-(2-valerylhydrazino)-2,5-dihydro-1,2,4-triazine (1.176 g) was obtained by reduction of the corresponding triazine compound (2.714 g) with 10% palladium on carbon (0.5 g) in a similar manner to that of Example 11-(4). m.p. 178°~179° C. (recrystallized from isopropyl alcohol).

IR (Nujol): 3230, 3050, 1625, 1610 cm$^{-1}$

NMR (DMSO-d$_6$, δ): 0.88 (3H, t, J=7 Hz), Ca 1.0~1.72 (4H, m), 1.17 (3H, d, J=6.5 Hz), 2.11 (2H, t, J=7 Hz), 4.54 (1H, q, J=6.5 Hz), 7.12~7.52 (3H, m), 7.52~7.78 (2H, m), Ca 8.4 (2H, b.s.)

EXAMPLE 19

(1) A solution of ethyl chloroformate (3.689 g) in methylene chloride (10 ml) was added dropwise to a stirred solution of N-ethoxycarbonylglycine (4.998 g) and triethylamine (3.434 g) in methylene chloride (60 ml) under cooling in 5 minutes, and the stirring was continued for 5 minutes under cooling. To the solution of the mixed anhydride was added a solution of 3-hydrazino-5-methyl-6-phenyl-1,2,4-triazine (3.417 g) in chloroform (40 ml) and reacted in a similar manner to that of Example 17-(1). The reaction mixture was washed with water, dried over magnesium sulfate, and evaporated under reduced pressure. The residue was dissolved in ethanol (50 ml) and a solution of sodium hydroxide (1.6 g) in water (10 ml) was added dropwise to the solution with stirring under ice cooling in 5 minutes. After stirring for 30 minutes at room temperature, the solution was evaporated, and the residue was dissolved in a small amount of water. The solution was salted out and extracted with ethyl acetate. The extract was washed with a saturated aqueous solution of sodium chloride, dried over magnesium sulfate, and evaporated. The residue was dissolved in chloroform containing a small amount of ethanol and the solution was chromatographed on silica gel (50 g). The eluent with a mixture of chloroform and ethanol (30:1) gave a colorless solid of 3-[2-(N-ethoxycarbonylglycyl)hydrazino]-5-methyl-6-phenyl-1,2,4-triazine (1.872 g).

NMR (DMSO-d$_6$, δ): 1.17 (3H, t, J=7Hz), 2.41 (3H, s), 3.76 (2H, d, J=6 Hz), 4.03 (2H, q, J=7 Hz), 7.2~7.8 (6H, m), 9.43 (1H, b.s.), 10.02 (1H, b.s.)

(2) A solution of 3-[2-(N-ethoxycarbonylglycyl)hydrazino]-5-methyl-6-phenyl-1,2,4-triazine (1.815 g) in ethanol (32 ml) containing anhydrous hydrogen chloride was shaken with 5% palladium on carbon (0.4 g) under atmosphere of hydrogen gas at room temperature. After the theoretical amount of hydrogen gas was absorbed, the catalyst was filtered off, and the filtrate was evaporated. The residue was dissolved in water and made alkaline with an aqueous solution of sodium bicarbonate under ice cooling. The resulting precipitates were collected by filtration, washed with water, dried, and recrystallized from ethanol to give colorless crystals of 3-[2-(N-ethoxycarbonylglycyl)hydrazino]-5-methyl-6-phenyl-2,5-dihydro-1,2,4-triazine (1.198 g), m.p. 144.5°~145.5° C.

IR (Nujol): 3600, 3400, 3220, 1710, 1665, 1625, 1610 cm$^-$

NMR (DMSO-d$_6$, δ): 1.17 (3H, t, J=7 Hz), 1.18 (3H, d, J=6.5 Hz), Ca 3.3 (1H, b.s.), 3.64 (2H, d, J=6 Hz), 4.01 (2H, q, J=7 Hz), 4.54 (1H, q, J=6.5 Hz), 7.3~7.53 (3H, m), 7.53~7.8 (2H, m), Ca 7.1 (1H, b.s.), Ca 9.0 (2H, b.s.)

Anal. Calcd. for C$_{15}$H$_{20}$N$_6$O$_3$: C, 54.21; H, 6.07; N, 25.29. Found: C, 53.62; H, 6.43; N, 25.48.

EXAMPLE 20

(1) The reaction of ethyl chloroformate (2.441 g) with N-t-butoxycarbonylglycine (3.938 g) in methylene chloride under ice cooling gave a solution comprising the mixed acid anhydride, which was reacted with 3-hydrazino-5-methyl-6-phenyl-1,2,4-triazine (3.015 g) in a similar manner to that of Example 17-(1) to give 3-[2-(N-t-butoxycarbonylglycyl)hydrazino]-5-methyl-6-phenyl-1,2,4-triazine (4.068 g). The purification was conducted with column chromatography on silica gel (80 g) using a mixture of methylene chloride and methanol (30:1) as an eluent.

NMR (CDCl$_3$, δ): 1.45 (9H, s), 2.43 (3H, s), 4.03 (2H, d, J=6 Hz), 5.79 (1H, t, J=6 Hz), 7.4~7.6 (5H, m), 8.0 (1H, b.s.), 9.45 (1H, b.s.)

(2) Sodium borohydride (0.494 g) was reacted with 3-[2-(N-t-butoxycarbonylglycyl)hydrazino]-5-methyl-6-phenyl-1,2,4-triazine (3.58 g) in similar manner to that of Example 2-(2) to give a solution containing the corresponding 2,5-dihydro-1,2,4-triazine compound. The reaction mixture was concentrated under reduced pressure after addition of dry ice. The residue was dissolved in chloroform. The solution was washed with a saturated aqueous solution of sodium chloride, dried over magnesium sulfate and evaporated. The resultant oily residue (3.71 g) was dissolved in ethanol (30 ml). To the solution was added a saturated ethanolic solution of hydrogen chloride (30 ml) under ice cooling, and then the stirring was continued for 2.5 hours at the same temperature. The reaction mixture was evaporated. The resultant solid was recrystallized from 10% hydrochloric acid to give colorless crystals of 3-(2-glycylhydrazino)-5-methyl-6-phenyl-2,5-dihydro-1,2,4-triazine dihydrochloride (2.054 g), m.p. 251°~253° C. (decomp.).

IR (Nujol): 2800~3200 (broad), 1650 cm$^{-1}$

NMR (D₂O, δ): 1.37 (3H, d, J=6.5 Hz), 4.21 (2H, s), 4.91 (1H, q, J=6.5 Hz), 7.4~7.8 (5H, m)

Anal. Calcd. for $C_{12}H_{16}N_6O \cdot 2HCl$: C, 43.25; H, 5.44; N, 25.22. Found: C, 42.96; H, 5.59; N, 25.46.

EXAMPLE 21

(1) 3-(2-Benzoylhydrazino)-5-methyl-6-phenyl-1,2,4-triazine (3.58 g) was obtained by reacting benzoyl chloride (1.17 g) with 3-hydrazino-5-methyl-6-phenyl-1,2,4-triazine (2.45 g) in the presence of triethylamine (1.23 g) in a similar manner to that of Example 14-(1). This substance was crystallized with diisopropyl ether.

NMR (DMSO-d₆, δ): 2.45 (3H, s), 7.61 (8H, m), 8.06 (2H, m), 9.66 (1H, s), 10.69 (1H, s)

(2) Sodium borohydride (1.98 g) and 3-(2-benzoylhydrazino)-5-methyl-6-phenyl-1,2,4-triazine (3.45 g) was reacted in a similar manner to that of Example 2-(2). The reaction mixture was diluted with diisopropyl ether and the resultant precipitates were collected, washed successively with water, methanol and diisopropyl ether, and recrystallized from a mixture of ethanol, chloroform and water to give colorless crystals of 3-(2-benzoylhydrazino)-5-methyl-6-phenyl-2,5-dihydro-1,2,4-triazine (1.76 g), m.p. 217.5°–218° C. (decomp.).

NMR (DMSO-d₆, δ): 1.23 (3H, d, J=6.5 Hz), 4.63 (1H, q, J=6.5 Hz), 7.33~7.62 (6H, m), 7.67~8.06 (4H, m)

Anal. Calcd. for $C_{17}H_{17}N_5O$: C, 66.43; H, 5.58; N, 22.79. Found: C, 66.42; H, 5.42; N, 22.45.

EXAMPLE 22

(1) A solution of methyl isocyanate (0.92 g) in methylene chloride (3 ml) was added dropwise to a stirred solution of 3-hydrazino-5-methyl-6-phenyl-1,2,4-triazine (3 g) in methylene chloride (20 ml) at room temperature. The reaction mixture was diluted with diisopropyl ether (30 ml). The resultant precipitates were collected by filtration to give a solid of 5-methyl-3-(4-methylsemicarbazido)-6-phenyl-1,2,4-triazine (3.8 g).

NMR (DMSO-d₆, δ): 2.43 (3H, s), 2.62 (3H, d, J=5 Hz), 6.46 (1H; br.q.; J=5 Hz), 7.6 (5H, m), 8.06 (1H, s), 9.24 (1H, s)

(2) 5-Methyl-3-(4-methylsemicarbazido)-6-phenyl-1,2,4-triazine (3.8 g) was reacted with sodium borohydride (1.5 g) in methanol. The precipitates in the reaction mixture were collected by filtration, washed with water and with methanol, and then dissolved in dimethyl sulfoxide. To the solution was added water. The resultant precipitates were collected by filtration, washed with water and ethanol, and then dried to give pale yellow powder of 5-methyl-3-(4-methylsemicarbazido)-6-phenyl-2,5-dihydro-1,2,4-triazine (2.48 g), mp 214° C. (decomp.).

NMR (DMSO-d₆, δ): 1.18 (3H, d, J=6.8 1 Hz), 2.65 (3H, d, J=4.5 Hz), 4.57 (1H, q, J=6.8 Hz), 6.01 (1H, br.d., J=4.5 Hz), 7.48 (3H, m), 7.7 (2H, m), 9.1 (2H, m)

Anal. Calcd. for $C_{12}H_{16}N_6O$: C, 55.37; H, 6.25; N, 32.29. Found: C, 55.76; H, 6.27; N, 32.08.

EXAMPLE 23

(1) 5-Methyl-6-phenyl-3-(4-phenylsemicarbazido)-1,2,4-triazine (2.88 g) was obtained by reacting phenyl isocyanate (1.13 g) with 3-hydrazino-5-methyl-6-phenyl-1,2,4-triazine (1.87 g) in a similar manner to that of Example 22-(1).

NMR (DMSO-d₆, δ): 2.45 (3H, s), 6.95~7.80 (10H, m), 8.34 (1H, s), 8.87 (1H, s), 9.37 (1H, s)

(2) 5-Methyl-6-phenyl-3-(4-phenylsemicarbazido)-2,5-dihydro-1,2,4-triazine (1.63 g) was obtained by reduction of the corresponding triazine compound (2.86 g) in a similar manner to that of Example 2-(2). m.p. 175° C. (decomp.) (recrystallized from a mixture of ethanol and diisopropyl ether).

NMR (DMSO-d₆, δ): 1.21 (3H, d, J=6.3 Hz), 4.58 (1H, q, J=6.3 Hz), 6.8~7.56 (8H, m), 7.57~7.78 (2H, m), 7.8~8.4 (2H, m), 9.2 (1H, b.s.)

Anal. Calcd. for $C_{17}H_{18}N_6O$: C, 63.51; H, 5.82; N, 25.45. Found: C, 63.22; H, 5.78; N, 25.13.

EXAMPLE 24

(1) C.hydrochloric acid (1 drop) was added to a stirred solution of 3-hydrazino-5-methyl-6-phenyl-1,2,4-triazine (4.12 g) and propionaldehyde (4 ml) in methanol (15 ml) at room temperature, and the stirring was continued for 5 minutes. The reaction mixture was evaporated and the resultant residue was triturated with diethyl ether. The precipitates were collected by filtration to give 5-methyl-6-phenyl-3-(2-propylidenehydrazino)-1,2,4-triazine (3.89 g).

NMR (CDCl₃, δ): 1.33 (3H, t, J=7.3 Hz), 2.40 (2H, m), 2.57 (3H, s), 7.50 (6H, m), 11.4 (1H, b.s.)

(2) 5-Methyl-6-phenyl-3-(2-propylidenehydrazino)-2,5-dihydro-1,2,4-triazine (1.98 g) was obtained by reduction of the corresponding triazine compound (2.85 g) in a similar manner to that of Example 11-(4).

m.p. 171°~173° C. (recrystallized from ethanol).

NMR (CDCl₃, δ): 1.12 (3H, t, J=6.8 Hz), 1.36 (3H, d, J=8.8 Hz). 2.32 (2H, d, q; J=6.0, 6.8 Hz), 4.60 (1H, q, J=8.8 Hz), 6.60 (1H, br.m), 7.24~7.44 (3H, m), 7.52~7.87 (3H, m), 9.64 (1H, br.m)

Anal. Calcd. for $C_{13}H_{17}N_5$: C, 64.44; H, 6.66; N, 28.91. Found: C, 64.12; H, 6.68; N, 28.76.

EXAMPLE 25

(1) A mixture of 4'-chloro-2-hydroxyiminopropiophenone (252.3 g), thiosemicarbazide (151.3 g), methanol (650 ml) water (300 ml), and acetic acid (9 ml) was refluxed for 31 hours with stirring. After cooling, the resulting precipitates were collected by filtration, washed successively with methanol, water and methanol, and then dried to give 4'-chloro-2-hydroxyiminopropiophenone thiosemicarbazone (298.88 g).

NMR (DMSO-d₆, δ): 2.16 (3H, s), 7.26 (2H, d, J=8.3 Hz), 7.60 (2H, d, J=8.3 Hz), 8.30 (1H, b.s.), 8.62 (1H, b.s.), 8.78 (1H, s), 11.77 (1H, s)

(2) A mixture of 4'-chloro-2-hydroxyiminopropiophenone thiosemicarbazone (113.21 g), potassium carbonate (128.71 g) and water (990 ml) was refluxed for 25 hours with stirring, and the reaction mixture was treated with activated charcoal and filtered by suction. To the filtrate was added dropwise methyl iodide (76 g) with stirring, and the stirring was continued for 15 minutes at room temperature. The resulting solid was collected by filtration, washed with water and dissolved in chloroform. The solution was treated with silica gel and filtered, and the filtrate was evaporated under reduced pressure. The residue was washed with diisopropyl ether and dried to give a solid of 6-(4-chlorophenyl)-5-methyl-3-methylthio-1,2,4-triazine (61.1 g).

NMR (CDCl₃, δ): 2.56 (3H, s), 2.73 (3H, s), 7.56 (4H, s)

(3) A solution of 6-(4-chlorophenyl)-5-methyl-3-methylthio-1,2,4-triazine (32.4 g) and hydrazine hydrate (40.8 g) in ethanol (110 ml) was heated for 2 hours. After cooling, the precipitates were collected by filtration, washed with ethanol, dried and recrystallized from ethanol to give 6-(4-chlorophenyl)-3-hydrazino-5-methyl-1,2,4-triazine (4.54 g).

NMR (DMSO-d$_6$, δ): 2.37 (3H, s), 4.38 (2H, m), 7.57 (4H, s), 8.66 (1H, m)

(4) 6-(4-Chlorophenyl)-3-hydrazino-5-methyl-1,2,4-triazine (4.36 g) was dissolved in ethanol (70 ml) containing anhydrous hydrogen chloride, and then hydrogenated over 5% palladium on carbon (0.73 g) under atmospheric pressure at room temperature. After the theoretical amount of hydrogen gas was absorbed, the catalyst was filtered off. The filtrate was evaporated under reduced pressure to give a residual solid, which was recrystallized from diluted hydrochloric acid to give colorless crystals of 6-(4-chlorophenyl)-3-hydrazino-5-methyl-2,5-dihydro-1,2,4-triazine hydrochloride (2.04 g), m.p. 207°~208° C.

NMR (DMSO-d$_6$, δ): 1.26 (3H, d, J=7 Hz), 4.88 (1H, q, J=7 Hz), 7.52 (2H, d, J=9 Hz), 7.83 (2H, d, J=9 Hz), 9.7 (1H, b.s.), 10.9 (1H, b.s.)

Anal. Calcd. for C$_{10}$H$_{12}$ClN$_5$.HCl: C, 43.81; H 4.78; N, 25.55. Found: C, 44.03; H, 4.90; N, 25.70.

EXAMPLE 26

(1) A mixture of 6-(4-chlorophenyl)-3-hydrazino-5-methyl-1,2,4-triazine (7 g), 2-iodomethylthio-2-imidazoline (8.11 g) and n-butanol (50 ml) was refluxed for 3 hours with stirring. After cooling, the mixture was evaporated under reduced pressure and the residue was dissolved in 1N hydrochloric acid. The solution was washed with ethyl acetate and made alkaline with an aqueous solution of potassium carbonate. The resultant precipitates were collected by filtration, washed with water, dried and recrystallized from methanol and then from ethanol to give dark red crystals of 6-(4-chlorophenyl)-3-[2-(2-imidazolin-2-yl)hydrazino]-5-methyl-1,2,4-triazine (1.53 g), m.p. 230°~231° C. (decomp.).

NMR (DMSO-d$_6$, δ): 2.32 (3H, s), 3.34 (4H, s), 7.58 (4H, s)

Anal. Calcd. for C$_{13}$H$_{14}$ClN$_7$: C, 51.40; H, 4.65; Cl, 11.67. Found: C, 51.58; H, 4.67; Cl, 11.70.

(2) 6-(4-Chlorophenyl)-3-[2-(2-imidazolin-2-yl)hydrazino]-5-methyl-2,5-dihydro-1,2,4-triazine dihydrochloride (2.18 g) was obtained by reduction of the corresponding triazine compound (2.53 g ) in a similar manner to that of Example 25-(4). m.p. 263°~267° C. (decomp.) (recrystallized from ethanol).

NMR (DMSO-d$_6$, δ): 1.32 (3H, d, J=6.7 Hz), 3.68 (4H, s), 4.98 (1H, q, J=6.7 Hz), 7.52 (2H, d, J=8.7 Hz), 7.87 (2H, d, J=8.7 Hz), 9.04 (2H, br.m.), 11.0 (3H, br.m.)

Anal. Calcd. for C$_{13}$H$_{16}$ClN$_7$.2HCl: C, 41.23; H, 4.79; N, 25.89. Found: C, 40.96; H, 4.70; N, 26.11.

EXAMPLE 27

(1) 2-Hydroxyimino-4'-methoxypropiophenone thiosemicarbazone (80.31 g) was obtained by reacting 2-hydroxymino-4'-methoxypropiophenone (92 g) with thiosemicarbazine (50 g) in a similar manner to that of Example 25-(1).

NMR (DMSO-d$_6$, δ): 2.15 (3H, s), 3.80 (3H, s), 7.10 (4H, m), 8.06 (1H, b.s.), 8.42 (1H, b.s.), 8.57 (1H, b.s.), 11.66 (1H, s)

(2) A mixture of 2-hydroxyimino-4'-methoxypropiophenone thiosemicarbazone (5.32 g), potassium carbonate (6.35 g) and water (50 ml) was treated in a similar manner to that of Example 25-(2), and then treated with activated charcoal. To the filtrate was added methyl iodide (6 g), and the mixture was stirred for 30 minutes at room temperature. The reaction mixture was extracted with ethyl acetate. The extract was washed with water, dried over sodium sulfate, treated with silica gel, and filtered. The filtrate was concentrated to dryness to give a residue, which was crystallized from diisopropyl ether. The resultant crystals were collected by filtration, washed with diisopropyl ether and dried to give 6-(4-methoxyphenyl)-5-methyl-3-methylthio-1,2,4,-triazine (2.42 g).

NMR (CDCl$_3$, δ): 2.53 (3H, s), 2.67 (3H, s), 3.84 (3H, s), 6.96 (2H, d, J=9 Hz), 7.53 (2H, d, J=9 Hz)

(3) 3-Hydrazino-6-(4-methoxyphenyl)-5-methyl-1,2,4-triazine (5.65 g) was obtained by reacting hydrazine hydrate (8.5 g) with 6-(4-methoxyphenyl)-5-methyl-3-methylthio-1,2,4-triazine (7.1 g) in a similar manner to that of Example 25-(3).

NMR (DMSO-d$_6$, δ): 2.40 (3H, s), 3.84 (3H, s), 4.29 (2H, b.s.), 7.03 (2H, d, J=8.6 Hz), 7.53 (2H, d, J=8.6 Hz), 8.47 (1H, b.s.)

(4) 3-Hydrazino-6-(4-methoxyphenyl)-5-methyl-2,5-dihydro-1,2,4-triazine hydrochloride (2.38 g) was obtained by reduction of the corresponding triazine compound (3.0 g) in a similar manner to that of Example 25-(4). m.p. 112.5°~115° C. (recrystallized from water).

NMR (DMSO-d$_6$, δ): 1.27 (3H, d, J=6.7 Hz), 3.86 (3H, s), 4.91 (1H, q, J=6.7 Hz), 7.05 (2H, d, J=8.3 Hz), 7.80 (2H, d, J=8.3 Hz), 11.85 (1H, br.m.)

EXAMPLE 28

(1) A mixture of 5-methyl-3-methylthio-6-phenyl-1,2,4-triazine (2.17 g) and potassium hydroxide (1.04 g) in water (3 ml) was heated at 50°, to 53° C. for 45 minutes. After addition of methanol (4.5 ml), the mixture was heated at 60° C. for 3 hours. The reaction mixture was treated with activated charcoal after addition of water, and filtered by suction. The filtrate was concentrated to dryness and the residual solid was recrystallized from methanol to give crystals of potassium salt of 5-methyl-6-phenyl-1,2,4-triazine-3(2H)-one (2.22 g). A mixture of the above obtained potassium salt compound (6 g), n-butyl chloride (4.04 g) and potassium iodide (6.64 g) in methanol (60 ml) was refluxed for 7 hours. The reaction mixture was evaporated, and the residue was extracted with chloroform after addition of water. The extract was chromatographed on silica gel (30 g) using successively a mixture of diisopropyl ether and benzene (1:20), diisopropyl ether and chloroform as eluents. The eluates were combined, concentrated to dryness, and recrystallized from diisopropyl ether to give crystals of 2-n-butyl-5-methyl-6-phenyl-1,2,4-triazin-3(2H)-one 1.13 g).

NMR (CDCl$_3$, δ): 0.75~2.20 (7H, m), 2.47 (3H, s), 4.21 (2H, t, J=7.3 Hz), 7.50 (5H, s)

(2) 2-n-Butyl-5-methyl-6-phenyl-4,5-dihydro-1,2,4-triazin-3(2H)-one (0.69 g) was obtained by reacting sodium borohydride (0.54 g) with the above obtained triazine compound (0.91 g) in a similar manner to that of Example 2-(2). m.p. 90°~91.5° C. (recrystallized from diethyl ether).

NMR (CDCl$_3$, δ): 1.80~2.05 (10H, m), 3.67~4.03 (2H, m), 4.68 (1H; d, q; J=3.3, 6.7 Hz), 6.37 (1H, br.m.), 7.30~7.53 (3H, m), 7.60~7.85 (2H, m)

Anal. Calcd. for C$_{14}$H$_{19}$N$_3$O: C, 68.54; H, 7.81; N, 17.13. Found: C, 68.97; H, 7.94; H, 16.80.

EXAMPLE 29

(1) Potassium salt of 5-methyl-6-phenyl1,2,4-triazin-3(2H)-one (20 g) was dissolved in methanol (200 ml). Methyl iodide (37.8 g) was added thereto, and the solution was refluxed for 2.5 hours, and evaporated under reduced pressure. The resultant residue was washed with water and dissolved in chloroform. The solution was washed with water, dried over magnesium sulfate and concentrated to dryness. The residue was washed with ethyl acetate and dried to give 2,5-dimethyl-6-phenyl-1,2,4-triazin-3(2H)-one (12.11 g).

NMR (CDCl$_3$, $\delta$): 2.48 (3H, s), 3.86 (3H, s), 7.50 (5H, s)

(2) 2,5-Dimethyl-6-phenyl-4,5-dihydro-1,2,4-triazin-3(2H)-one (2.31 g) was obtained by reacting sodium borohydride (0.72 g) with 2,5-dimethyl-6-phenyl-1,2,4-triain-3(2H)-one (3.88 g) in a similar manner to that of Example 2-(2). m.p. 99.5°~101° c. (recrystallized from diisopropyl ether).

NMR (CDCl$_3$, $\delta$): 1.37 (3H, d, J=6.7 Hz), 3.46 (3H, s), 4.72 (1H, d,q; J=3.5, 6.7 Hz), 7.02 (1H, b.s.), 7.26~7.55 (3H, m), 7.63~7.86 (2H, m)

Anal. Calcd. for C$_{11}$H$_{13}$N$_3$O: C, 65.00; H, 6.45; N, 20.68. Found: C, 65.28; H, 6.39; N, 20.63.

EXAMPLE 30

A hot solution of 2,5-dimethyl-6-phenyl-1,2,4-triazin-3(2H)-one (5 g) in benzene (60 ml) was added dropwise to a stirred solution of methylmagnesium iodide prepared from methyl iodide (17.5 g) and magnesium turnings (3 g) in diethyl ether (80 ml) at room temperature. The solution was refluxed under heating for 40 minutes and then allowed to stand for 1 hour at room temperature. The solution was treated with a saturated aqueous solution of ammonium chloride to decompose excess Grignard reagent. The organic layer was separated, dried over magnesium sulfate, treated with activated charcoal, and evaporated to dryness. The resultant solid was recrystallized from a mixture of diisopropyl ether and chloroform to give 6-phenyl-2,5,5-trimethyl-4,5-dihydro-1,2,4-triazin-3(2H)-one (4.21 g), m.p. 128°~130° C.

NMR (CDCl$_3$, $\delta$): 1.46 (6H, s), 3.40 (3H, s), 6.58 (1H, b.s.), 7.39 (5H, s)

EXAMPLE 31

2,5-Dimethyl-6-phenyl-1,2,4-triazin-3(2H)-one (3.2 g) was added to a stirred solution of benzylmagnesium chloride prepared from benzyl chloride (9.99 g) and magnesium turnings (1.92 g) in diethyl ether (48 ml) at room temperature. The reaction mixture was treated in a similar manner to that of Example 30 to give 5-benzyl-2,5-dimethyl-6-phenyl-4,5-dihydro-1,2,4-triazin-3(2H)-one (2.6 g), m.p. 174.2°~175.3° C. recrystallized from a mixture of chloroform and diisopropyl ether).

NMR (CDCl$_3$, $\delta$): 1.36 (3H, s), 2.86 (1H, d, J=13.2 Hz), 3.21 (3H, s), 3.23 (1H, d, J=13.2 Hz), 5.77 (1H, b.s.), 7.27 (5H, s), 7.47 (5H, s)

Anal. Calcd. for C$_{18}$H$_{19}$N$_3$O: C, 73.69; H, 6.53; N, 14.32. Found: C, 74.12; H, 6.50; N, 14.28.

EXAMPLE 32

(1) A mixture of 4'-bromo-2-hydroxyiminopropiophenone (31 g), thiosemicarbazide (15.13 g), methanol (67 ml), water (31 ml) and acetic acid (1.1 ml) was refluxed for 31 hours with stirring. After cooling, the resultant precipitates were collected by filtration, washed successively with methanol, water and methanol, and then dried to give a solid of 4'-bromo-2-hydroxyiminiopropiophenone thiosemicarbazone (isomeric mixture, 37.88 g).

NMR (DMSO-d$_6$, $\delta$): 1.92 (Ca. 0.85H, s), 2.15 (Ca. 2.15H, s), 7.12 (2H, d, J=8 Hz), 7.62 (2H, d, J=8 Hz), 7.5~8.6 (2H, complex), 8.69 (Ca. 0.72H, s), 10.74 (Ca. 0.28H, s), 11.53 (Ca. 0.72H, s), 12.03 (Ca. 0.28H, s)

(2) A mixture of 4'-bromo-2-hydroxyiminopropiophenone thiosemicarbazine (37.73 g) and potassium carbonate (36.89 g) in water (296 ml) was refluxed for 1 day with stirring. After cooling, the mixture was filtered by suction and then methyl iodide (22.1 g) was added dropwise to the filtrate at room temperature with stirring. After 15 minutes, the precipitates were collected by filtration, washed with water, dried and recrystallized from ethanol to give 6-(4-bromophenyl)-5-methyl-3-methylthio-1,2,4-triazine (18.3 g).

NMR (DMSO-d$_6$, $\delta$): 2.5 (3H, s), 2.66 (3H, s), 7.67 (2H, d, J=8 Hz), 7.77 (2H, d, J=8 Hz)

(3) A mixture of 6-(4-bromophenyl)-5-methyl-3-methylthio-1,2,4-triazine (4.94 g), 20% aqueous solution of potassium hydroxide (10.8 ml), water (20 ml) and methanol (61 ml) was heated at 60° C. for 4 hours with stirring. The reaction mixture was evaporated, and the residue was dissolved in methanol (100 ml). To the solution was added portionwise sodium borohydride (0.946 g) with stirring under ice cooling. After stirring for 2.5 hours at room temperature, the mixture was treated with 10% hydrochloric acid to decompose excess sodium borohydride and concentrated to a small volume. The resultant precipitates were collected by filtration, washed with water and dried to give 6-(4-bromophenyl)-5-methyl-4,5-dihydro-1,2,4-triazi-3(2H)-one (4.46 g).

NMR (DMSO-d$_6$, $\delta$): 1.18 (3H, d, J=6.8 Hz), 4.61 (1H; d,q; J=3.4, 6.8 Hz), 7.41 (1H, br.s.), 7.60 (4H, m), 10.0 (1H, br.s.)

EXAMPLE 33

(1) 2'-Chloro-2-hydroxyiminopropiophenone thiosemicarbazone (24.59 g) was obtained by reacting 2'-chloro-2-hydroxyiminopropiophenone (23.24 g) with thiosemicarbazide (13.93 g), in methanol (57 ml), water (26 ml) and acetic acid (1 ml) in a similar manner to that of Example 32-(1).

NMR (DMSO-d$_6$, $\delta$): 2.17 (3H, s), 7.16~7.59 (4H, m), 8.08 (1H, b.s.), 8.58 (2H, b.s.), 11.79 (1H, s)

(2) A mixture of 2'-chloro-2-hydroxyiminopropiophenone thiosemicarbazine (21.25 g) and potassium carbonate (23.87 g) in water (200 ml) was refluxed for 23.5 hours with stirring. After cooling, the mixture was filtered by suction and then methyl iodide (14.5 g) was added to the filtrate at room temperature with stirring. After 15 minutes, the separated oily layer was extracted with ethyl acetate, and the extract was washed with water, dried over magnesium sulfate, and evaporated under reduced pressure to give dark-brown oil of 6-(2-chlorophenyl)-5-methyl-3-methylthio-1,2,4-triazine (14.52 g).

NMR (DMSO-d$_6$, $\delta$): 2.3 (3H, s), 2.66 (3H, s), 7.53 (4H, m)

(3) 6-(2-Chlorophenyl)-5-methyl4,5-dihydro-1,2,4-triazin-3(2H)-one(0.73 g) was obtained from 6-(2-chlorophenyl)-5-methyl-3-methylthio-1,2,4-triazine (1.52 g) in a similar manner to that of Example 32-(3), and recrystallized from ethanol.

NMR (DMSO-d$_6$, δ): 1.08 (3H, d, J=6.5 Hz), 4.38 (1H; d,q; J=2, 6.5 Hz), 7.2~7.6 (5H, m), 9.89 (1H, b.s.)

EXAMPLE 34

5,6-Dimethyl-3-methylthio-1,2,4-triazine (2.48 g) was reacted with potassium hydroxide (1.792 g), and the reaction mixture was reduced by sodium borohydride (0.907 g) in a similar manner to that of Example 32-(3). The above reaction mixture was concentrated, and the residue was treated with 10% hydrochloric acid and then evaporated under reduced pressure. The resultant solid was extracted with a mixture of chloroform and methanol. The extract was evaporated, and the resultant residue was dissolved in a small amount of water. The solution was passed through a column of DIAION NP-20 (Trademark, manufactured by Mitsubishi Chemical Industries Ltd.) (100 ml) using water and then a mixture of methanol and water (1:1) as eluents. The eluate with aqueous methanol was evaporated under reduced pressure and the residue was dissolved in acetone under reflux. The solution was treated with activated charcoal and filtered. The filtrate was evaporated and resultant residue was recrystallized from ethanol to give 5,6-dimethyl-4,5-dihydro-1,2,4-triazin-3(2H)-one (0.719 g), m.p. 200°~102.5° C.

IR (Nujol): 3220, 3080, 1685 cm$^{-1}$

NMR (DMSO-d$_6$, δ): 1.16 (3H, d, J=7 Hz), 1.85 (3H, s), 3.30 (1H; d,q; J=2, 7 Hz), 7.0 (1H, b.s.), 9.36 (1H, b.s.)

Anal. Calcd. for C$_5$H$_9$N$_3$O: C; 47.23; H, 7.13; N, 33.05. Found: C, 47.09; H, 7.14; N, 32.72.

EXAMPLE 35

(1) A mixture of 2-hydroxyiminopropiophenone (150 g) and thiosemicarbazine (90 g) in acetic acid (500 ml) was heated at 60° C. for 60 hours with stirring. After cooling, water was added to the reaction mixture. The resultant precipitates were collected by filtration, washed successively with water, methanol and diisopropyl ether, and dried to give 2-hydroxyiminopropiophenone thiosemicarbazone (188.2 g).

NMR (DMSO-d$_6$, δ): 2.17 (3H, s) 7.15~7.40 (2H, m), 7.40∫7.70 (3H, m), 8.16 (1H, b.s.), 8.37 (1H, s) 8.66 (1H, b.s.), 11.68 (1H,s)

(2) A mixture of 2-hydroxyiminopropiophenone thiosemicarbazone (42 g) and sodium hydroxide (14 g) in water (150 ml) was refluxed for 5 hours under nitrogen atmosphere. The reaction mixture was treated with activated charcoal and filtered by suction. The filtrate was acidified with diluted hydrochloric acid, and the resultant precipitates were collected by filtration, washed with water and dried. The above obtained crude product (6.59 g) was dissolved in methanol (150 ml), and the solution was filtered by suction. The filtrate was concentrated under reduced pressure, and the residue was crystallized from diisopropyl ether, collected by filtration, washed with a mixture of methanol and diisopropyl ether, and dried to give 5-methyl-6-pnehyl-1,2,4-triazine-3(2H)-thione which have methanol of crystallization.

NMR (CDCl$_3$, δ): 1.64 (3H, s), 3.31 (3H, s), 7.34~7.56 (3H, m), 7.56~8.00 (3H, m), 9.83 (1H, b.s.)

(3) Sodium borohydride (0.71 g) and 5-methyl-6-phenyl-1,2,4-triazine-3(2H)-thione which have methanol of crystallization (4.03 g) were reacted in tetrahydrofuran according to a similar manner to that of EXAMPLE 2:(2). The reaction mixture was treated with a mixture of 1N-hydrochloric acid and water, and then extracted with ethyl acetate. The extract was washed successively with 1N hydrochloric acid, brine, an aqueous solution of sodium carbonate and brine, dried over magnesium sulfate and concentrated to dryness. The resultant solid was washed with diisopropyl ether and recrystallized from ethanol to give 5-methyl-6-phenyl-4,5-dihydro-1,2,4-triazine-3(2H)-thione (1.48 g), mp 213°~214.5° C.

NMR (DMSO-d$_6$, δ): 1.19 (3H, d, J=5 Hz), 4.64 (1H; d,q; J=3.6, 6.5 Hz), 7.38~7.60 (3H, m), 7.60∫7.92 (2H, m), 9.20 (1H, b.s.), 11.43 (1H. b.s.)

Anal. Calcd. for C$_{10}$H$_{11}$N$_3$S: C, 58.51; H, 5.40; N, 20.47; S, 15.62. Found: C, 58.27; H, 5.32; N, 20.30; S, 15.73.

(4) Methyl 5-bromo-4-oxopentanoate (1.29 g) was added to a solution of 5-methyl-6-phenyl-4,5-dihydro-1,2,4-triazine-3(2H)-thione (1.26 g) and sodium methoxide (0.4 g) in methanol (18 ml), and stirring was continued for 1 hour at room temperature. The solution was evaporated under reduced pressure and the residue was chromatographed on silica gel (50 g). The eluate with a mixture of benzene and ethyl acetate (4:1) was evaporated to dryness and the residual solid was recrystallized from a mixture of ethyl acetate and diisopropyl ether to give rystals of 3-(4-methoxycarbonyl-2-oxobutylthio)-5-methyl-6-phenyl, 2,5-dihydro-1,2,4-triazine (0.75 g), m.p. 128.5° to 129.5° C.

NMR (CDCl$_3$δ): 1.27 (3H, d, J=7 Hz), 2.56 (4H, m), 3.23, 3.50 (2H, ABq, J=12.5 Hz), 3.73 (3H, s), 4.85 (1H, q, J=7 Hz), 7.3~7.6 (3H, m), 7.73~7/93 (2H, m)

Anal Calcd. for C$_{16}$H$_{19}$N$_3$O$_3$S: C, 57.64; H, 5.74; N, 12.60. Found: C, 57.91; H, 5.75; N, 12.48.

EXAMPLE 36

(1) A solution of triethylamine (15 g) in chloroform (15 ml) was added dropwise to a stirred mixture of 2-aminopropiophenone hydrochloride (12 g) and chloroform (65 ml) at ice bath temperature in 10 minutes. To the stirred mixture was added dropwise a solution of ethyl chloroformate (8 g) in chloroform (20 ml) under the same conditions and then stirring was continued for 4 hours at ice bath temperature. The solution was evaporated under reduced pressure and the residue was dissolved in a mixture of ethyl acetate and water. The organic layer was separated, washed successively with a saturated aqueous solution of sodium bicarbonate, water, 5% hydrochloric acid, and water, dried over magnesium sulfate, and evaporated under reduced pressure to give an oil containing the object compound. The above obtained product was purified by column chromatography on silica gel (200 g) using a mixture of diisopropyl ether and chloroform (1:4) as an eluent to give an oil of 2-ethoxycarbonylaminopropiophenone (10.48 g).

NMR (CDCl$_3$, δ): 1.26 (3H, t, J=7.2 Hz), 1.45 (3H, d, J=7.2 Hz), 4.16 (2H, q, J=7.2 Hz), 5.36 (IH, quintet, J=7.2 Hz), 5.83 (1H, br. d., J=7.2 Hz), 7.6 (3H, m), 8.03 (2H, m)

(2) A mixture of 2-ethoxycarbonylaminopropiophenone (5 g) and hydrazine (3.5 g) in n-butanol (40 ml) was refluxed for 4 hours. The reaction mixture was evaporated, and the residue was chromatographed on silica gel (400 g) using a mixture of chloroform and methanol (100:1) as an eluent. The first fraction was evaporated to give 2-ethoxycarbonylaminopropiophenone hydrazone (4.5 g).

NMR (CDCl$_3$, δ): 1.24 (3H, d, J=7.1 Hz), 1.24 (3H, t, J=7.1 Hz), 4.11 (2H, q, J=7.1 Hz), 4.55 (1H, quintet, J=7.1 Hz), 5.20 (2H, br. m.), 5.77 (1H, br. d, J=7.1 Hz), 7.4~7.6 (5H, m)

On the other hand, the second fraction was concentrated to dryness to give 5-methyl-6-phenyl-4,5-dihydro-1,2,4-triazin-3(2H)-one (0.22 g).

NMR (DMSO-d$_6$, δ): 1.21 (3H, d, J=6.4 Hz), 4.68 (1H; d,q, J=3.3, 6.4 Hz), 7.3~7.6 (4H, m), 7.6~7.9 (2H, m), 10.07 (1H, b.s.)

(3) A mixture of 2-ethyxycarbonylaminopropiophenone hydrazone (4.05 g) and hydrazine hydrate (Lb 7.27 g) in n-butanol (48 ml) was refluxed for 72 hours and evaporated under reduced pressure. The residue was dissolved in chloroform, washed with water, dried over sodium sulfate and concentrated to dryness. The residual solid was washed with diisopropyl ether, dissolved in ethyl acetate and concentrated to dryness. The resulting solid was recrystallized from a mixture of benzene and ethanol to give 5-methyl-6-phenyl-4,5-dihydro-1,2,4-triazin-3(2H)-one (0.72 g), m.p. 213.5°~214° C. The NMR data of this compound was identical to that of (2).

Anal. Cald. for C$_{10}$H$_{11}$N$_3$O: C, 63.48; H, 5,86; N, 22.21. Found: C, 63.71; H, 5,72; N, 22.52.

EXAMPLE 37

(1) 4'-Bromo-2-ethoxycarbonylaminopropiophenone (4.49 g) was obtained from 4'-bromo-2-aminopropiophenone hydrochloride (8.76 g) in a similar manner to that of Example 36-(1). m.p. 103°~104.5° C. (crystallized from diisopropyl ether).

NMR (CDCl$_3$, δ): 1.23 (3H, t, J=7.1 Hz), 1.38 (3H, d, J=7.3 Hz), 4.11 (2H, q, J=7.1 Hz), 5.24 (1H, quintet, J=7.3 Hz), 5.67 (1H, br.d., J=7.59 (2H, d, J=9 Hz), 7.84 (2H, d, J=9 Hz)

(2) A mixture of 4'-bromo-2-ethoxycarbonylaminopropiophenone (4.29 g), hydrazine hydrate (8 g) and n-butanol (50 ml) was refluxed under heating for 68 hours. The solution was evaporated to dryness, and the resultant residue was dissolved in a mixture of chloroform and methanol. The solution was washed with water and the washings were extracted with chloroform. The combined organic layer was dried over magnesium sulfate and evaporated to dryness. The resultant residue was washed with diisopropyl ether and recrystallized from ethanol to give colorless crystals of 6-(4-bromophenyl)-5-methyl-4,5-dihydro-1,2,4-triazin-3(2H)-one (1.68 g), m.p. 213.5°~215° C.

NMR (DMSO-d$_6$, δ): 1.18 (3H, d, J=6.8 Hz), 4.61 (1H; d,q; J=3.4, 6.8 Hz), 7.41 (1H, br.s.), 7.60 (4H, m), 10.0 (1H, br.s.)

Anal Calcd. for C$_{10}$H$_{10}$BrN$_3$O: C, 44.80, H, 3,76; N, 15.67. Found: C, 45.18; H, 3.69; N, 15.93.

EXAMPLE 38

Triethylamine (4.33 g) was added dropwise to a stirred solution of 2-amino-4'-methoxypropiophenone hydrochloride (4.57 g) in chloroform (50 ml) under ice cooling and then ethyl chloroformate (2.33 g) was added dropwise to the solution. After stirring for 1.5 hours, the solution was washed successively with water, 1N hydrochloric acid and brine, dried over sodium sulfate and concentrated to dryness. To the residue was added a mixture of hydrazine hydrate (11 g) and n-butanol (50 ml), and the mixture was refluxed for 91 hours. After cooling, the mixture was evaporated and the residue was dissolved in chloroform. The solution was washed with water and brine, dried over sodium sulfate and concentrated to dryness. The residual solid was washed with diisopropyl ether, dried and recrystallized from ethanol to give 6-(4-metoxyphenyl)-5-methyl-4,5-dihydro-1,2,4-triazin-3(2H)-one (2.68 g), m.p. 216.°~218° C.

NMR (DMSO-d$_6$, δ): 1.21 (3H, d, J=7Hz), 3.80 (3H, s), 4.64 (1H; d,q; J=3.3, 7 Hz), 7.01 (2H, d, J=9 Hz), 71.44 (1H, b.s.), 7.74 (2H, d, J=9 Hz), 10.66 (1H, b.s.)

Anal. Calcd. for C$_{11}$H$_{13}$N$_3$O$_2$: C, 60.26; H, 5,98; N, 19.17. Found: C, 60.41; H, 5,91; N, 19.35.

EXAMPLE 39

(1) 4'-Chloro-2-ethoxycarbonylaminopropiophenone (4.3 g) was obtained from 2-amino-4'-chloro propiophenone hydrochloride (9.07 g) in a similar manner to that of Example 36-(1). m.p. 94°~96° C. (crystallized from diisopropyl ether).

NMR (CDCl$_3$, δ): 1.23 (3H, t, J=7.2 Hz), 1.40 (3H, d, J=7.2 Hz), 4.12 (2H, q, J=7.2 Hz), 5.25 (1H, quintet, J=7.2 Hz), 5.68 (1H, br.d., J=7.2 Hz), 7.45 (2H, d, J=8.8 Hz), 7.93 (2H, d, J=8.8 Hz)

(2) 6-(4-Chlorophenyl)-5-methyl-4,5-dihydro-1,2,4-triazin-3(2H)-one (3.01 g) was obtained by reacting 4'-chloro-2-ethoxycarbonylaminopropiophenone (5.42 g) with hydrazine hydrate (11 g) in n-butanol (65 ml) in a similar manner to that of Example 37-(2). m.p. 221°~222° C. (recrystallized from ethanol).

NMR (DMSO-d$_6$, δ): 1.18 (3H, d, J=6.5 Hz), 4.64 (1H; d,q; J=3.2, 6.5 Hz), 7.43 (2H, d, J=8.9 Hz), 7.5 (1H, b.s.), 7.74 (2H, d, J=8.9 Hz), 10.04 (1H, b.s.)

Anal. Calcd. for C$_{10}$H$_{10}$ClN$_3$O: C, 53.70; H, 4.51; N, 18.79. Found: C, 53.92; H, 4,38; N, 18.74.

EXAMPLE 40

(1) 2-Ethoxycarbonylamino-4'-methylpropiophenone (8.64 g) was obtained from 2-amino-4'-methylpropiophenone hydrochloride (7.83 g) in a similar manner to that of Example 36-(1). m.p. 79°~81° C. (crystallized from diisopropyl ether).

NMR (CDCl$_3$, δ): 1.24 (3H, t, J=7.2 Hz), 1.40 (3H, d, J=7.2 Hz), 2.41 (3H, s), 4.13 (2H, q, J=7.2 Hz), 5.29 (1H, quintet, J=7.2 Hz), 5.70 (1H, b.s.), 7.30 (2H, d, J=8.1 Hz), 7.90 (2H, d, J=8.1 Hz)

(2) 5-Methyl-6-(4-tolyl)-4,5-dihydro-1,2,4-triazin-3(2H)-one (4.22 g) was obtained by reacting 2-ethoxycarbonylamino-4'-methylpropiophenone (7.86 g) with hydrazine hydrate (16.9 g) in a similar manner to that of Example 37-(2). m.p. 245.5°~246° C. (recrystallized from ethanol).

NMR (DMSO-d$_6$, δ): 1.19 (3H, d, J=6.7 Hz), 2.32 (3H, s), 4.61 (1H; d,q; J=1.6, 6.7 Hz), 7.18 (2H, d, J=8.2 Hz), 7.3 (1H, br.s.), 7.59 (2H, d, J=8.2 Hz), 9.88 (1H, br.s.)

Anal Calcd. for C$_{11}$H$_{13}$N$_3$O: C, 65.00; H, 6,45; N, 20.68. Found: C, 64.88; H, 6.38; N, 20.62.

EXAMPLE 41

(1) Triethylamine (1 ml) was added to a solution of 2-aminopropiophenone hydrochloride (0.93 g) and dimethyl cyanodithioimidocarbonate (0.73 g) in methanol (3 ml), and the mixture was refluxed for 15 minutes and evaporated under reduced pressure. The residue was dissolved in chloroform and the solution was washed with water, dried over sodium sulfate and concentrated under reduced pressure. The residue was dissolved in a small amount of ethyl acetate and diluted with diisopropyl ether. The resultant precipitates were collected by filtration, washed with diisopropyl ether and dried to give 2-(3-cyano-2-methyl-1-isothioureido)propiophenone (0.99 g).

NMR (CDCl$_3$, δ): 1.55 (3H, d, J=7 Hz), 2.67 (3H, s), 5.57 (1H, q, J=7 Hz), 7.15 (1H, b.s.), 7.66 (3H, m), 8.0 (2H, m)

(2) Hydrazine hydrate (4.55 g) was added to a solution of 2-(3-cyano-2-methyl-1-isothioureido)propiophenone (5.43 g) in methanol (20 ml), and the mixture was allowed to stand at room temperature for 1 hour. After addition of catalytic amount of sodium methoxide to the solution, the mixture was allowed to stand at room temperature for 2 hours with occasional shaking. The resultant precipitates were collected, washed successively with methanol, water and methanol and dried. Thus obtained product was dissolved with dimethylformamide (25 ml), the solution was filtered by suction and then water (25 ml) was added thereto little by little. After cooling, the resultant precipitates were collected by filtration, washed successively with ethanol, water and ethanol, and dried to give 3-cyanoamino-5-methyl-6-phenyl-2,5-dihydro-1,2,4-triazine (2.37 g), m.p. 244.5°~245° C. (decomp.).

NMR (DMSO-d$_6$, δ): 1.27 (3H, d, J=6.8 Hz), 4.75 (1H, q, J=6.8 Hz), 7.40~7.67 (3H, m), 7.67~7.90 (2H, m), 9.0 (1H, b.s.), 11.0 (1H, b.s.)

Anal. Calcd. for C$_{11}$H$_{11}$N$_5$: C, 61.96; H, 5.20; N, 32.84. Found: C, 61.69; H, 4.96; N, 32.73.

EXAMPLE 42

(1) A solution of triethylamine (5.455 g) in chloroform (5 ml) was added dropwise to a stirred solution of 2-amino-1-(2-thienyl)-1-propanone hydrochloride (2.585 g) in chloroform (26 ml) under ice cooling in 5 minutes. To the mixture was added dropwise a solution of ethyl chloroformate (2.929 g) in chloroform (7 ml), and the stirring was continued for 2 hours under the same conditions. The reaction mixture was evaporated, and the residue was dissolved in a mixture of ethyl acetate and water. The organic layer was separated, washed successively with a saturated aqueous solution of sodium bicarbonate, water, 5% hydrochloric acid and water, dried over magnesium sulfate and evaporated to give an oil of 2-(2-ethoxycarbonylaminopropionyl)thiophene (2.752 g).

NMR (CDCl$_3$, δ): 1.25 (3H, t, J=7 Hz), 1.48 (3H, d, J=7 Hz), 4.14 (2H, q, J=7 Hz), 5.16 (1H, quintet, J=7 Hz), Ca. 5.6 (1H, b.s.), 7.1~7.3 (1H, m), 7.6~7.9 (2H, m)

(2) 5-Methyl-6-(2-thienyl)-4,5-dihydro-1,2,4-triazin-3(2H)-one (0.83 g) was obtained by reacting 2-(2-ethoxycarbonylaminopropionyl)thiophene (2.724 g) with hydrazine hydrate (6 g) in a similar manner to that of Example 37-(2). m.p. 213°~214.5° C. (decomp.) (recrystallized from ethanol).

IR (Nujol): 3200, 3100 (shoulder), 3070, 1690, 1665 cm$^{-1}$

NMR (DMSO-d$_6$, δ): 1.27 (3H, d, J=6 Hz), 4.58 (1H; octet; J=4, 6 Hz), 7.0~7.12 (1H, m), 7.32~7.6 (3H, m), 9.92 (1H, b.s.)

Anal. Calcd. for C$_8$H$_9$N$_3$OS: C, 49.21; H, 4.65; N, 21.52; S, 16.42. Found: C, 49.11; H, 4.47; N, 21.54; S, 16.15.

EXAMPLE 43

(1) 6-(4-Bromophenyl)-5-methyl-3-(1-methylhydrazino)-1,2,4-triazine (3.85 g) was obtained from 5-methyl-3-methylthio-6-(4-bromophenyl)-1,2,4-triazine (4.7 g) according to similar manner to that of Example 13-(1).

NMR (DMSO-d$_6$, δ): 2.37 (3H, s), 3.3 (3H, s), 5.02 (2H, s), 7.48 (2H, d, J=8 Hz), 7.63 (2H, d, J=8 Hz)

(2) 6-(4-Bromophenyl)-5-methyl-3-(1-methylhydrazino)-2,5-dihydro-1,2,4-triazine (1.77 g) was obtained from the above obtained compound (3.85 g) according to similar manner to that of Example 11-(4). m.p. 144.5° to 146.5° C. (from benzene).

NMR (CDCl$_3$, δ): 1.18 (3H, d, J=6 Hz), 3.17 (3H, s), 3.63 (2H, b.s.), 4.66 (1H, q, J=6 Hz), 7.54 (4H, m), 9.23 (1H, b.s.)

Anal. Calcd. for C$_{11}$H$_{14}$BrN$_5$: C, 44.61; H, 4.76; N, 23.65. Found: C, 44.85; H, 4.67; N, 23.88.

EXAMPLE 44

(1) 6-(4-Bromophenyl)-3-hydrazino-5-methyl-1,2,4-triazine (3.13 g) was obtained from 6-(4-bromophenyl)-5-methyl-3-methylthio-1,2,4-triazine (4 g) according to similar manner to that of Example 25-(3).

NMR (DMSO-d$_6$, δ): 2.37 (3H, s), 4.38 (2H, b.s.), 7.54 (2H, d, J=8.5 Hz), 7.71 (2H, d, J=8.5 Hz), 8.68 (1H, b.s.)

(2) 6-(4-Bromophenyl)-3-hydrazino-5-methyl-2,5-dihydro-1,2,4-triazine hydrochloride (1.65 g) was obtained from the above obtained compound (3.07 g) according to similar manner to that of Example 25-(4). m.p. 207° to 209° C. (from ethanol).

NMR (DMSO-d$_6$, δ): 1.26 (3H, d, J=6.9 Hz), 3.31 (2H, b.s.), 4.85 (1H, q, J=6.9 Hz), 7.68 (4H, b.s.), 8.1~10.0 (2H, b.s.), 10.2~12.2 (1H, b.s.)

Anal. Calcd. for C$_{10}$H$_{12}$BrN$_5$.HCl: C, 37.70; H, 4.11; N, 21.98. Found: C, 37.55; H, 4.10; N, 21.91.

EXAMPLE 45

(1) 3-(2-t-Butoxycarbonylhydrazino)-6-(4-chlorophenyl)-5-methyl-1,2,4-triazine (19.38 g) was obtained from 6-(4-chlorophenyl)-3-hydrazino-5-methyl-1,2,4-triazine (16.23 g) according to similar manner to that of Example 13-(2).

NMR (DMSO-d$_6$, δ): 1.41 (9H, s), 2.37 (3H, s), 7.57 (4H, m), 8.95 (1H, b.s.), 9.30 (1H, b.s.)

(2) 3-(2-t-Butoxycarbonylhydrazino)-6-(4-chlorophenyl)-5-methyl-2,5-dihydro-1,2,4-triazine (3.61 g) was obtained from the above obtained compound (19.38 g) according to similar manner to that of Example 2-(2). m.p. 213.5° C. (decomp). (recrystallized from a mixture of ethanol and chloroform).

NMR (DMSO-d$_6$, δ): 1.13 (3H, d, J=7 Hz), 1.41 (9H, s), 4.52 (1H, q, J=7 Hz), 7.43 (2H, d, J=9 Hz), 7.73 (2H, d, J=9 Hz)

Anal. Calcd. for C$_{15}$H$_{20}$ClN$_5$O$_2$: C, 53.33; H, 5.97; N, 20.73. Found: C, 52.97; H, 5.89; N, 20.86.

EXAMPLE 46

(1) 3-(2-Acetylhydrazino)-6-(4-chlorophenyl)-5-methyl-1,2,4-triazine (3.15 g) was obtained from 6-(4-chlorophenyl)-3-hydrazino-5-methyl-1,2,4-triazine (3 g) according to similar manner to that of Example 15-(1).

NMR (DMSO-d$_6$, δ): 1.92 (3H, s), 2.38 (3H, s), 7.55 (4H, m), 9.31 (1H, b.s.), 9.85 (1H, b.s.)

(2) 3-(2-Acetylhydrazino)-6-(4-chlorophenyl)-5-methyl-2,5-dihydro-1,2,4-triazine (2.04 g) was obtained from the above obtained compound (3.11 g) according to similar manner to that of Example 15-(2). m.p. 208° C. (decomp.)

NMR (DMSO-d$_6$, δ): 1.35 (3H, d, J=6.5 Hz), 1.81 (3H, s), 3.3 (2H, b.s.), 4.52 (1H, q, J=6.5 Hz), 7.42 (2H, d, J=9 Hz), 7.73 (2H, d, J=9 Hz), 9.0 (1H, b.s.)

Anal. Calcd. for C$_{12}$H$_{14}$ClN$_5$O: C, 51.53; H, 5.04; N, 25.04. Found: C, 51.38; H, 4.96; N, 25.33.

EXAMPLE 47

(1) A solution of acetylacetone (2.415 g) in methanol (10 ml) was added to a mixture of 6-(4-chlorophenyl)-3-hydrazino-5-methyl-1,2,4-triazine (4.946 g) and acetic acid (3 drops) in methanol (20 ml), and the solution was refluxed for 2 hours with stirring and allowed to stand at room temperature. The resultant crystals were collected by filtration, washed with cold methanol, and dried to give 6-(4-chlorophenyl)-3-(3,5-dimethyl-pyrazol-1-yl)-5-methyl-1,2,4-triazine (5.354 g), m.p. 151° to 152.5° C.

IR (Nujol): 1596, 1576, 1525 cm$^{-1}$

NMR (DMSO-d$_6$, δ): 2.23 (3H, s), 2.58 (6H, s), 6.21 (1H, s), 7.57 (2H, d, J=8 Hz), 7.77 (2H, d, J=8 Hz)

Anal. Calcd. for C$_{15}$H$_{14}$ClN$_5$: C, 60.10; H, 4.71; N, 23.96. Found: C, 60.37; H, 4.63; N, 23.65.

(2) Crude 6-(4-chlorophenyl)-3-(3,5-dimethylpyrazol-1-yl)-5-methyl-2,5-dihydro-1,2,4-triazine hydrochloride (2.27 g) was obtained from the above compound (2.396 g) according to similar manner to that of Example 2-(2). The oily crude product was crystallized from a mixture of ethanol and 10% hydrochloric acid to give white crystals of the object compound.

NMR (DMSO-d$_6$, δ): 1.46 (3H, d, J=7 Hz), 2.32 (3H, s), 2.72 (3H, s), 5.31 (1H, q, J=7 Hz), 6.47 (1H, s), 7.67 (2H, d, J=8.5 Hz), 8.07 (2H, d, J=8.5 Hz)

EXAMPLE 48

(1) 2-Hydroxyimino-4'-nitropropiophenone thiosemicarbazone (3.3 g) was obtained as syn- and anti-isomeric mixture by reacting 2-hydroxyimino-4'-nitropropiophenone (5.2 g) with thiosemicarbazide (2.9 g) in a similar manner to that of Example 25-(1). The ratio of isomers A and B is about 1:2.

isomeric isomer A: 1.92 (s), 7.86 (d, J=8 Hz), 8.13 (d, J=8 Hz), 10.92 (b.s.), 12.07 (b.s.)

isomeric isomer B: 2.16 (s), 7.43 (d, J=8 Hz), 8.2 (d, J=8 Hz), 9.17 (b.s), 11.53 (s)

(2) A mixture of 2-hydroxyimino-4'-nitropropiophenone thiosemicarbazone (15.8 g) and potassium carbonate (17.09 g) in water (145 ml) was refluxed for 30 minutes with stirring. After cooling, the mixture was filtered by suction and then methyl iodide (10.37 g) was added dropwise to the filtrate at room temperature with stirring. The resulting precipitates were collected by filtration, washed with water, and dried. The residue was purified by column chromatography on silica gel (100 g) with methylene chloride as an eluent to give yellow powder of 5-methyl-3-methylthio-6-(4-nitrophenyl)-1,2,4-triazine (6.49 g).

NMR (CDCl$_3$, δ): 2.59 (3H, s), 2.73 (3H, s), 7.84 (2H, d, J=8 Hz), 8.37 (2H, d, J=8 Hz)

(3) Crude 5-methyl-6-(4-nitrophenyl)-4,5-dihydro-1,2,4-triazin-3(2H)-one (1.18 g) was obtained from the above compound (5.43 g) according to similar manner to that of Example 32-(3). The crude product was successively recrystallized from acetonitrile and then acetone to give crystals of the object compound. m.p. 257.5° to 259.5° C.

IR (Nujol): 3260, 1715, 1680 cm$^{-1}$

NMR (DMSO-d$_6$, δ): 1.22 (3H, d, J=6.4 Hz), 4.74 (1H, d, q; J=2.8, 6.4 Hz), 7.57 (1H, b.s.), 7.8~8.4 (4H, m), 10.34 (1H, s)

Anal. Calcd. for C$_{10}$H$_{10}$N$_4$O$_3$: C, 51.06; H, 4.29; N, 23.82. Found: C, 50.86; H, 4.21; N, 23.79.

EXAMPLE 49

(1) 6-(2-hydroxyimino-1-thiosemicarbazonopropyl)-1-methyl-2-oxo-1,2,3,4-tetrahydroquinoline (0.34 g) was obtained from 6-(2-hydroxyiminopropionyl)-1-methyl-2-oxo-1,2,3,4-tetrahydroquinoline (1 g) according to similar manner to that of Example 25-(1).

NMR (DMSO-d$_6$, δ): 2.14 (3H, s), 2.4~3.1 (4H, m), 3.25 (3H, s), 7.0~7.3 (3H, m), 8.07 (1H, b.s), 8.47 (1H, s), 8.5 (1H, b.s.), 11.68 (1H, s)

(2) 5-Methyl-6-(1-methyl-2-oxo-1,2,3,4-tetrahydroquinolin-6-yl)-3-methylthio-1,2,4-triazine (26.05 g) was obtained from the above compound (56.53 g) according to similar manner to that of Example 25-(2).

NMR (CDCl$_3$, δ): 2.58 (3H, s), 2.69 (3H, s), Ca. 2.5~3.2 (4H, m), 3.4 (3H, s), 7.1 (1H, d, J=9 Hz), 7.4~7.68 (2H, m)

(3) Potassium salt of 5-methyl-6-(1-methyl-2-oxo-1,2,3,4-tetrahydroquinolin-6-yl)-1,2,4-triazin-3(2H)-one was obtained from the above compound (6 g) in a similar manner to that of Example 28-(1). Thus obtained potassium salt compound was dissolved in water (30 ml), and DIAION HP-20 (Trademark, manufactured by Mitsubishi Chemical Ind. Ltd.) (20 ml) was added thereto. After stirring for 1.5 hours at room temperature, the mixture was filtered by suction and washed with water. The filtrate was concentrated to half volume under reduced pressure and sodium borohydride (3.168 g) was added portionwise to the stirred solution after addition of methanol (55 ml). After the reduction was finished, the reaction mixture was treated with 10% hydrochloric acid to decompose excess sodium borohydride and concentrated to a small volume. The resulting precipitates were collected by filtration, washed with water, and recrystallized from ethanol to give 5-methyl-6-(1-methyl-2-oxo-1,2,3,4-tetrahydroquinolin-6-yl)-4,5-dihydro-1,2,4-triazin-3(2H)-one. m.p. 240° to 242.5° C.

NMR (CDCl$_3$, δ): 1.41 (3H, d, J=6.9 Hz), 2.46~3.15 (4H, m), 3.34 (3H, s), 4.70 (1H; d, q; J=3.2, 6.9 Hz), 6.79 (1H, b.s.), 6.95 (1H, d, J=9.5 Hz), 7.51 (1H, d,d; J=2.5, 9.5 Hz), 7.56 (1H, d, J=2.5 Hz), 8.65 (1H, d, J=3.2 Hz)

Anal. Calcd. for C$_{14}$H$_{16}$N$_4$O$_2$: C, 61.75; H, 5.92. Found: C, 61.80; H, 6.11.

EXAMPLE 50

(1) 2-(2-Hydroxyiminopropionyl)pyridine thiosemicarbazone (58.3 g) was obtained from 2-(2-hydroxyiminopropionyl)pyridine (43.2 g) according to similar manner to that of Example 25-(1).

NMR (DMSO-d$_6$, δ): 2.23 (3H, s), 7.3~7.7 (2H, m), 7.8~8.2 (2H, m), 8.5~8.8 (2H, m), 11.5 (1H, s), 11.6 (1H, s)

(2) Crude 5-methyl-3-methylthio-6-(2-pyridyl)-1,2,4-triazine was obtained from the above compound (57.64 g) according to similar manner to that of Example 25-(2). The crude product was purified by column chromatography on silica gel (700 g) with a mixture of benzene and ethyl acetate (10:1) as an eluent to give yellow crystals (33.09 g) of the object compound.

NMR (CDCL$_3$, δ): 2.67 (3H, s), 2.76 (3H, s),7.16~7.46 (1H, m), 7.63~8.23 (2H, m), 8.56~8.74 (1H, m)

(3) A solution of the potassium salt of 5-methyl-6-(2-pyridyl)-1,2,4-triazin-3(2H)-one in aqueous methanol was obtained from the above compound (5.09 g) according to similar manner to that of Example 32-(3). Thus obtained solution was diluted with water (65 ml) and treated with sodium borohydride (0.78 g) with stirring under ice cooling. After stirring for 1.5 hours, the solution was evaporated under reduced pressure and the residue was dissolved in diluted hydrochloric acid. The solution was washed with ethyl acetate, concentrated under reduced pressure, and the residue was made alkaline with an aqueous solution of potassium carbonate. The resulting precipitates were collected by filtration, washed with water, and recrystallized from ethanol to give crystals of 5-methyl-6-(2-pyridyl)-4,5-dihydro-1,2,4-triazin-3(2H)-one (2.1 g). m.p. 212° to 213.5° C.

NMR (DMSO-$d_6$, $\delta$): 1.21 (3H, d, J=6.7 Hz), 4.86 (1H; d,q; J=3, 6.7 Hz), 7.2~7.53 (2H, m), 7.62~8.05 (2H, m), 8.54 (1H, broad d, J=5 Hz), 10.12 (1H, b.s.)

Anal. Calcd. for $C_9H_{10}N_4O$: C, 56.83; H, 5.30; N, 29.46. Found: C, 56.89; H, 5.21; N, 29.80.

EXAMPLE 51

(1) 5-Methyl-3-(1-methylhydrazino)-6-(2-pyridyl)-1,2,4-triazine (4.3 g) was obtained from the object compound of Example 50-(2) (5 g) according to similar manner to that of Example 13-(1).

NMR (DMSO-$d_6$, $\delta$): 2.57 (3H, s), 3.34 (3H, s), 5.1 (2H, b.s.), 7.25~7.58 (1H, m), 7.8~8.06 (2H, m), 8.53~8.73 (1H, m)

(2) 5-Methyl-3-(1-methylhydrazino)-6-(2-pyridyl)-2,5-dihydro-1,2,4-triazine (1.26 g) was obtained from the above compound (3.36 g) according to similar manner to that of Example 2-(2). m.p. 152° to 154° C. (from benzene).

NMR (CDCl$_3$, $\delta$): 1.25 (3H, d, J=6.7 Hz), 3.17 (3H, s), 5.08 (1H, q, J=6.7 Hz), 7.04~7.35 (1H, m), 7.63 (1H, m), 7.99 (1H, m), 8.54 (1H, m)

Anal. Calcd. for $C_{10}H_{14}N_6$: C, 55.03; H, 6.47; N, 38.50. Found: C, 54.92; H, 6.45; N, 38.55.

EXAMPLE 52

(1) 3-Hydrazino-5-methyl-6-(2-pyridyl)-1,2,4-triazine (3.8 g) was obtained from the object compound of Example 50-(2) (5 g) according to similar manner to that of Example 13-(1).

NMR (DMSO-$d_6$, $\delta$): 2.58 (3H, s), 4.45 (2H, b.s.), 7.36~7.56 (1H, m), 7.8~8.1 (2H, m), 8.6~8.9 (1H, m), 8.8 (1H, b.s.)

(2) 3-(2-t-Butoxycarbonylhydrazino)-5-methyl-6-(2-pyridyl)-1,2,4-triazine (5 g) was obtained from the above compound (4.3 g) according to similar manner to that of Example 13-(2).

NMR (CDCl$_3$, $\delta$): 1.49 (9H, s), 2.71 (3H, s), 6.99 (1H, b.s.), 7.47~7.24 (2H, m), 7.7~7.9 (1H, m), 8.0~8.1 (1H, m), 8.6~8.7 (1H, m)

(3) 3-(2-t-Butoxycarbonylhydrazino)-5-methyl-6-(2-pyridyl)-2,5-dihydro-1,2,4-triazine (4.35 g) was obtained from the above compound (5.4 g) according to similar manner to that of Example 2-(2). m.p. 197° C. (decomp.) (from methanol).

NMR (DMSO-$d_6$, $\delta$): 1.16 (3H, d, J=6.5 Hz), 1.40 (9H, s), 4.81 (1H, q, J=6.5 Hz), 7.2~7.4 (1H, m), 7.7~8.0 (2H, m), 8.4~8.6 (1H, m), Anal. Calcd. for $C_{14}H_{20}N_6O_2$: C, 55.25; H, 6.62; N, 27.61. Found: C, 55.13; H, 6.40; N, 27.76.

EXAMPLE 53

(1) 3'-Chloro-2-hydroxyiminopropiophenone thiosemicarbazone (51.6 g) was obtained from 3'-chloro-2-hydroxyiminopropiophenone (58.36 g) according to similar manner to that of Example 25-(1).

NMR (DMSO-$d_6$, $\delta$): 2.17 (3H, s), 7.1~7.6 (4H, m), 8.02 (1H, b.s.), 8.54 (1H, b.s.), 8.79 (1H, s), 11.68 (1H, s)

(2) Crude 6-(3-chlorophenyl)-5-methyl-3-methylthio-1,2,4-triazine was obtained from the above compound (51.27 g) according to similar manner to that of Example 33-(2). Thus obtained crude product was purified by column chromatography on silica gel (900 g) with benzene as an eluent to give an oil (25.89 g) of the object compound.

NMR (CDCl$_3$, $\delta$): 2.51 (3H, s), 2.66 (3H, s), 7.2~7.6 (4H, m)

(3) Potassium salt of 6-(3'-chlorophenyl)-5-methyl-1,2,4-triazin-3(2H)-one was obtained from the above compound (5.05 g) according to similar manner to that of Example 32-(3). The potassium salt was dissolved in water (210 ml), and DIAION HP-20 (Trademark, manufactured by Mitsubishi Chemical Industries Ltd.) (20 ml) was added to the solution. After stirring for 1.5 hours at room temperature, the mixture was filtered by suction and washed with water. The filtrate was concentrated to half volume under reduced pressure and sodium borohydride (1.324 g) was added portionwise to the stirred solution after addition of methanol (55 ml). After the reduction was finished, the mixture was treated with 10% hydrochloric acid to decompose excess sodium borohydride and concentrated to a small volume. The resulting precipitates were collected by filtration, washed with water, and recrystallized from ethanol to give white crystals of 6-(3-chlorophenyl)-5-methyl-4,5-dihydro-1,2,4-triazin-3(2H)-one (1.98 g). m.p. 206.5° to 208° C.

IR (Nujol): 3210, 3090, 1695 cm$^{-1}$

NMR (DMSO-$d_6$, $\delta$): 1.22 (3H, d, J=6.8 Hz), 4.68 (1H; d,q; J=3.2, 6.8 Hz), 7.3~7.8 (5H, m), 10.12 (1H, b.s.)

Anal. Calcd. for $C_{10}H_{10}ClN_3O$: C, 53.70, H, 4.51; N, 18.79. Found: C, 53.98; H, 4.37; N, 19.10.

EXAMPLE 54

(1) 6-(3-Chlorophenyl)-5-methyl-3-(1-methylhydrazino)-1,2,4-triazine (5.0 g) was obtained from the object compound of Example 53-(2) (7.31 g) according to similar manner to that of Example 9-(1).

NMR (DMSO-$d_6$, $\delta$): 2.42 (3H, s), 3.36 (3H, s), 5.09 (2H, b.s.), 7.5~7.76 (4H, m)

(2) 6-(3-Chlorophenyl)-5-methyl-3-(1-methylhydrazino)-2,5-dihydro-1,2,4-triazine (1.74 g) was obtained from the above compound (5 g) according to similar manner to that of Example 11-(4). m.p. 115° to 117° C. (from benzene).

NMR (CDCl$_3$, $\delta$): 1.21 (3H, d, J=7 Hz), 3.15 (3H, s), 3.63 (2H, b.s.), 4.65 (1H, q, J=7 Hz), 7.2~7.8 (4H, m), 9.0 (1H, b.s.)

Anal. Calcd. for $C_{11}H_{14}ClN_5$: C, 52.49; H, 5.61; N, 27.82. Found: C, 52.44; H, 5.57; N, 28.12.

EXAMPLE 55

(1) 6-(3-Chlorophenyl)-3-hydrazino-5-methyl-1,2,4-triazine (3.65 g) was obtained from the object compound of Example 53-(2) (6.34 g) according to similar manner to that of Example 13-(1).

NMR (DMSO-d$_6$, δ): 2.37 (3H, s), 4.4 (2H, b.s.), 7.48~7.75 (4H, m), 8.67 (1H, b.s.)

(2) 6-(3-Chlorophenyl)-3-hydrazino-5-methyl-2,5-dihydro-1,2,4-triazine hydrochloride (1.84 g) was obtained from the above compound (3.63 g) according to similar manner to that of Example 25-(4). mp 207° to 208.5° C. (from a mixture of ethanol, diisopropylether, and tetrahydrofuran).

NMR (DMSO-d$_6$, δ): 1.26 (3H, d, J=6.5 Hz), 3.5 (2H, b.s.), 4.92 (1H, q, J=6.5 Hz), 7.43~7.95 (4H, m), 9.7 (1H, b.s.), 11.8 (1H, b.s.)

Anal. Calcd. for C$_{10}$H$_{12}$ClN$_5$.HCl: C, 43.81; H, 4.78; N, 25.55. Found: C, 43.77; H, 4.78; N, 25.51.

EXAMPLE 56

(1) A solution of dimethyl N-cyanodithioimidocarbonate (2.65 g) in methylene chloride (15 ml) was added to a solution of 3-hydrazino-5-methyl-6-phenyl-1,2,4-triazine (3.52 g) in methanol (20 ml) and stirring was continued for 40 hours at room temperature. The resultant precipitates were collected by filtration, washed with methanol, and dried to give 3-(5-amino-3-methylthio-1,2,4-triazol-1-yl)-5-methyl-6-phenyl-1,2,4-triazine (4.67 g).

NMR (CDCl$_3$, δ): 2.64 (3H, s), 2.75 (3H, s), 7.41 (2H, b.s.), 7.59 (5H, m)

(2) 3-(5-Amino-3-methylthio-1,2,4-triazol-1-yl)-5-methyl-6-phenyl-2,5-dihydro-1,2,4-triazine is obtained from the compound obtained in the above (1) in a similar manner to that of Example 1-(2).

EXAMPLE 57

(1) 5-Methyl-3-(4-methylthiosemicarbazido)-6-phenyl-1,2,4-triazine (280 mg) was obtained from 3-hydrazino-5-methyl-6-phenyl-1,2,4-triazine (211 mg) according to similar manner to that of Example 22-(1).

NMR (CDCl$_3$-DMSO-d$_6$, δ): 2.45 (3H, s), 2.99 (3H, d, J=4 Hz), 7.50 (5H, s), 7.85 (1H, q, J=4 Hz), 9.21 (2H, b.s.)

(2) Methyl iodide (0.39 g) was added to a mixture of 5-methyl-3-(4-methylthiosemicarbazido)-6-phenyl-1,2,4-triazine (0.25 g) and 0.5N sodium hydroxide solution (4 ml) and stirring was continued for 30 minutes at room temperature. The mixture was extracted with chloroform, and the extract was washed with water, dried over magnesium sulfate, and evaporated in vacuo. The residue was purified by column chromatography on silica gel (15 g) with ethyl acetate as an eluent to give crystals of 3-(4,S-dimethylisothiosemicarbazido)-5-methyl-6-phenyl-1,2,4-triazine (0.14 g).

NMR (CDCl$_3$, δ): 2.46 (6H, s), 2.95 (3H, b.s.), 7.49 (5H, s)

(3) 3-(4,S-Dimethylisothiosemicarbazido)-5-methyl-6-phenyl-2,5-dihydro-1,2,4-triazine is obtained from compound obtained in the above (2) in a similar manner to that of Example 1-(2).

EXAMPLE 58

(1) 6-(4-Chlorophenyl)-3-(2-hydroxyethylamino)-5-methyl-1,2,4-triazine (4.99 g) was obtained from 6-(4-chlorophenyl)-5-methyl-3-methylthio-1,2,4-triazine (6 g) according to similar manner to that of Example 6-(1).

NMR (DMSO-d$_6$, δ): 2.33 (3H, s), 3.28 (1H, s), 3.4~3.7 (4H, m), 4.67 (1H, t, J=5 Hz), 7.53 (4H, s)

(2) Crude 6-(4-chlorophenyl)-3-[N-formyl-N-(2-formyloxyethyl)amino]-5-methyl-1,2,4-triazine was obtained from the above compound (4.88 g) according to similar manner to that of Example 16-(1). The crude product was dissolved in a small amount of benzene and chromatographed on silica gel (80 g). The eluate with a mixture of benzene and ethyl acetate (10:1) was evaporated under reduced pressue and the residue was triturated with a mixture of diethyl ether and diisopropylether to give crystals (3.27 g) of the object compound.

NMR (CDCl$_3$, δ): 2.60 (3H, s), 4.50 (4H, s), 7.54 (4H, s), 8.0 (1H, s), 9.92 (1H, s)

(3) 6-(4-Chlorophenyl)-3-[N-formyl-N-(2-formyloxyethyl)amino]-5-methyl-2,5-dihydro-1,2,4-triazine is obtained from the compound obtained in the above (2) in a similar manner to that of Example 1-(2).

EXAMPLE 59

(1) 6-(4-Chlorophenyl)-5-methyl-3-[2-(methylamidino)hydrazino]-1,2,4-triazine (0.06 g) was obteined from the object compound of Example 25-(3) (1.198 g) according to similar manner to that of Example 26-(1).

NMR (DMSO-d$_6$, δ): 2.26 (3H, s), 2.65 (3H, s), 7.5 (4H, s)

(2) 6-(4-Chlorophenyl)-5-methyl-3-[2-(methylamidino)hydrazino]-2,5-dihydro-1,2,4-triazine is obtained from the compound obtained in the above (1) in a similar manner to that of Example 1-(2).

EXAMPLE 60

3-(2-Amidinohydrazino)-6-(4-chlorophenyl)-5-methyl-1,2,4-triazine (0.39 g) was obtained from the object compound of Example 25-(3) (1.52 g) and methylthioamidine hydriodic acid (1.75 g) according to similar manner to that of Example 26-(1).

NMR (DMSO-d$_6$, δ): 2.27 (3H, s), 7.57 (4H, s)

EXAMPLE 61

(1) 6-(4-Chlorophenyl)-3-(2-formylhydrazino)-5-methyl-1,2,4-triazine (3.16 g) was obtained from the object compound of Example 25-(3) (5.64 g) according to similar manner to that of Example 16-(1). mp 208° to 209.5° C. (from aqueous ethanol).

NMR (DMSO-d$_6$, δ): 2.37 (3H, s), 7.55 (4H, s), 8.13 (1H, s), 9.77 (2H, b.s.)

Anal. Calcd. for C$_{11}$H$_{10}$ClN$_5$O: C, 50.11; H, 3.82; N, 26.56; Cl, 13.45; Found: C, 49.85; H, 3.93; N, 26.73; Cl, 13.32.

(2) 6-(4-Chlorophenyl)-3-(2-formylhydrazino)-5-methyl-2,5-dihydro-1,2,4-triazine is obtained from the compound obtained in the above (1) in a similar manner to that of Example 1-(2).

EXAMPLE 62

(1) Crude 5-methyl-3-(1-methylhydrazino)-6-(1-methyl-2-oxo-1,2,3,4-tetrahydroquinolin-6-yl)-1,2,4-triazine was obtained from the object compound of Example 49-(2) (0.5 g) according to similar manner to that of Example 13-(1). The crude product was purified by column chromatography on silica gel (10 g) with a mixture of ethyl acetate, chloroform, and methanol (10:10:1) as an eluent to give the object compound (0.05 g).

NMR (CDCl$_3$, δ): 2.44 (3H, s), Ca. 2.4~3.13 (4H, m), 3.34 (3H, s), 3.42 (3H, s), Ca. 4.1 (2H, b.s.), 7.01 (1H, d, J=9.5 Hz), 7.3~7.55 (2H, m)

(2) 5-Methyl-3-(1-methylhydrazino)-6-(1-methyl-2-oxo-1,2,3,4-tetrahydroquinolin-6-yl)-2,5-dihydro-1,2,4-triazine is obtained from the compound obtained in the above (1) in a similar manner to that of Example 1-(2).

EXAMPLE 63

(1) 3-Hydrazino-5-methyl-6-(1-methyl-2-oxo-1,2,3,4-tetrahydroquinolin-6-yl)-1,2,4-triazine (7.3 g) was obtained from the object compound of Example 49-(2) (8.25 g) according to similar manner to that of Example 13-(1).

NMR (DMSO-$d_6$, $\delta$): 2.4 (3H, s), Ca. 2.5~2.72 (2H, m), 2.84~3.06 (2H, m), 3.32 (3H, s), 4.37 (2H, b.s.), 7.20 (1H, d, J=8 Hz), 7.4~7.6 (2H, m), 8.58 (1H, b.s.)

(2) Crude 3-(2-t-butoxycarbonylhydrazino)-5-methyl-6-(1-methyl-2-oxo-1,2,3,4-tetrahydroquinolin-6-yl)-1,2,4-triazine was obtained from the above compound (7.2 g) according to similar manner to that of Example 13-(2). The crude product was purified by column chromatography on silica gel (150 g) with ethyl acetate as an eluent to give pale yellow crystals of the object compound (6.83 g).

NMR (DMSO-$d_6$, $\delta$): 1.40 (9H, s), 2.40 (3H, s), Ca. 2.5~3.1 (4H, m), 3.26 (3H, s), 7.07~7.61 (3H, m), 8.91 (1H, b.s.), 9.2 (1H, b.s.)

(3) 3-(2-t-Butoxycarbonylhydrazino)-5-methyl-6-(1-methyl-2-oxo-1,2,3,4-tetrahydroquinolin-6-yl)-2,5-dihydro-1,2,4-triazine is obtained from the compound obtained in the above (2) in a similar manner to that of Example 1-(2).

EXAMPLE 64

(1) 4'-Methyl-2-hydroxyiminopropiophenone thiosemicarbazone (3.28 g) was obtained by reacting 4'-methyl-2-hydroxyiminopropiophenone (2.66 g) with thiosemicarbazide (1.78 g) according to a similar manner to that of Example 35-(1).

IR (Nujol): 3420, 3330, 3250, 3150, 1600, 1490, 1460 cm$^{-1}$ (2) 5-Methyl-6-(p-tolyl)-1,2,4-triazine-3(2H)-thione (3.71 g) was obtained by treating the above compound (5 g) with potassium carbonate (6.1 g) in water (44 ml) according to a similar manner to that of Example 35-(2).

IR (Nujol): 3150 (shoulder), 3110, 1600 (broad), 1625 cm$^{-1}$ (3) 4,5-Dihydro-5-methyl-6-(p-tolyl)-1,2,4-triazine-3(2H)-thione (1.32 g) was obtained by treating the above compound (3 g) with sodium borohydride (0.5 g) according to a similar manner to that of Example 35-(3).

NMR (DMSO-$d_6$, $\delta$): 1.20 (3H, d, J=8 Hz), 2.35 (3H, s), 4.65 (1H, m), 7.31 (2H, d, J=8 Hz), 7.72 (2H, d, J=8 Hz), 9.24 (1H, m), 11.37 (1H, s)

mp 278°~284° C. (dec.)

Anal. Calcd. for $C_{11}H_{13}N_3S$: C, 60.24; H, 5.97; N, 19.16. Found: C, 60.24; H, 6.02; N, 19.17.

EXAMPLE 65

(1) 6-(4-Chlorophenyl)-5-methyl-1,2,4-triazine-3(2H)-thione (2.6 g) was obtained by treating 4'-chloro-2-hydroxyiminopropiophenone thiosemicarbazone (4 g) with potassium carbonate (4.5 g) in water (33 ml) according to a similar manner to that of Example 35-(2).

IR (Nujol): 3150, 1560, 1460, 1375, 1245 cm$^{-1}$ (2) 6-(4-Chlorophenyl)-4,5-dihydro-5-methyl-1,2,4-triazine-3(2H)-thione (1.12 g) was obtained by treating the above obtained compound (2.5 g) with sodium borohydride (0.4 g) in methanol (125 ml) according to a similar manner to that of Example 35-(3). mp 254°~260° C. (dec.) [recrystallized from a mixture of chloroform and ethanol (1:1)]

NMR (DMSO-$d_6$, $\delta$): 1.20 (3H, d, J=6.5 Hz), 4.65 (1H, m), 7.49 (2H, d, J=9 Hz), 7.80 (2H, d, J=9 Hz), 9.28 (1H, m), 11.36 (1H, m)

Anal. Calcd. for $C_{10}H_{10}ClN_3S$: C, 50.10; H, 4.20; N, 17.53. Found: C, 50.14; H. 4.17; N, 17.54.

EXAMPLE 66

(1) 6-(4-Methoxyphenyl)-5-methyl-1,2,4-triazine-3(2H)-thione (3.97 g) was obtained by treating 2-hydroxyimino-4'-methoxypropiophenone thiosemicarbazone (5.32 g) with potassium carbonate (6.1 g) in water (44 ml) according to a similar manner to that of Example 35-(2).

IR (Nujol): 3150, 1605, 1510, 1455 cm$^{-1}$ (2) 4,5-Dihydro-6-(4-methoxyphenyl)-5-methyl-1,2,4-triazine-3-(2H)-thione (1.5 g) was obtained by treating the above compound (3.85 g) with sodium borohydride (0.63 g) according to a similar manner to that of Example 35-(3). mp 232°~235° C. (dec.) (recrystallized from a mixture of dimethylformamide and ethanol)

NMR (DMSO-$d_6$, $\delta$): 1.22 (3H, d, J=7 Hz), 3.78 (3H, s), 4.60 (1H, m), 6.95 (2H, d, J=8.5 Hz), 7.68 (2H, d, J=8.5 Hz), 9.10 (1H, m), 11.20 (1H, s)

Anal. Calcd. for $C_{11}H_{12}N_3OS$: C, 56.39; H, 5.16; N, 17.94. Found: C, 56.30; H, 5.51; N, 17.91.

EXAMPLE 67

(1) 6-(2-hydroxyimino-1-thiosemicarbazonopropyl)-2-oxo-1,2,3,4-tetrahydroquinoline (8.02 g) was obtained from 6-(2-hydroxyiminopropionyl)-2-oxo-1,2,3,4-tetrahydroquinoline (7.91 g) according to a similar manner to that of Example 32-(1).

NMR (DMSO-$d_6$, $\delta$): 2.1~3.1 (4H, m), 7.0~7.8 (3H, m), 10.23 (1H, b.s.), 1.97 (s), 2.17 (s) } (3H), 8.16 (b.s.), 8.53 (b.s.) } (2H), 8.6 (b.s.), 10.54 (s) } (1H), 11.73 (s), 12.17 (s) } (1H)

(2) 5-Methyl-3-methylthio-6-(2-oxo-1,2,3,4-tetrahydroquinolin-6-yl)-1,2,4-triazine (6.15 g) was obtained from the above compound (7.91 g) according to a similar manner to that of Example 32-(2).

NMR (DMSO-$d_6$, $\delta$): 2.3~3.1 (4H, m), 2.53 (3H, s), 2.63 (3H, s), 7.0 (1H, d, J=8 Hz), 7.38~7.61 (2H, m), 10.26 (1H, b.s.)

(3) 5-Methyl-6-(2-oxo-1,2,3,4-tetrahydroquinolin-6-yl)-4,5-dihydro-1,2,4-triazin-3(2H)-one (2.1 g) was obtained from the above compound (6 g) according to a similar manner to that of Example 32-(3). mp>300° C. (recrystallized from acetic acid)

NMR (DMSO-$d_6$, $\delta$): 1.19 (3H, d, J=7 Hz), Ca. 2.6 (2H, t, J=7 Hz), 2.92 (2H, t, J=7 Hz), 4.62 (1H; d,q; J=4, 7 Hz), 6.89 (1H, d, J=8 Hz), 7.3~7.7 (3H, m), 9.92 (1H, b.s.), 10.21 (1H, b.s.)

Anal. Calcd. for $C_{13}H_{14}N_4O_2$: C, 60.46; H, 5.46; N, 21.69. Found: C, 60.50; H, 5.55; N, 21.48.

EXAMPLE 68

(1) 1-Butyl-6-(2-hydroxyimino-1-thiosemicarbazonopropyl)-2-oxo-1,2,3,4-tetrahydroquinoline (8.54 g) was obtained from 1-butyl-6-(2-hydroxyiminopropionyl)-2-oxo-1,2,3,4-tetrahydroquinoline (8.61 g) according to a similar manner to that of Example 32-(1).

| NMR | (DMSO-d₆, δ): | 0.90 (3H, t, J = 6Hz), 1.46 (4H, b.s.), Ca. 2.5~3.1 (4H, m), 3.92 (2H, b.s.), 7.1~7.8 (3H, m), |
|---|---|---|
| | | 1.98 (s) ⎫ |
| | | 2.18 (s) ⎭ (3H), |
| 8.1 (b.s.) ⎫ | | 8.7 ⎫ |
| 8.58 (b.s.) ⎭ | 2H, | 10.62 (s) ⎭ (1H), |
| 11.71 (s) ⎫ | | |
| 12.10 (s) ⎭ | (1H) | |

(2) 6-(1-Butyl-2-oxo-1,2,3,4-tetrahydroquinolin-6-yl)-5-methyl-3-methylthio-1,2,4-triazine (4.15 g) was obtained from the above compound (8.30 g) according to a similar manner to that of Example 32-(2).

NMR (DMSO-d₆, δ): 0.92 (3H, t, J=6 Hz), Ca. 1.2~1.7 (4H, m), Ca. 2.5~2.8 (2H, m), 2.55 (3H, s), 2.65 (3H, s), 2.8~3.1 (2H, m), 3.95 (2H, t, J=6.5 Hz), 7.25 (1H, d, J=9 Hz), 7.5~7.73 (2H, m)

(3) 6-(1-Butyl-2-oxo-1,2,3,4-tetrahydroquinolin-6-yl)-5-methyl-4,5-dihydro-1,2,4-triazin-3(2H)-one (2.32 g) was obtained from the above compound (4 g) according to a similar manner to that of Example 32-(3). mp 132°~134° C. (recrystallized from 50% aqueous ethanol)

NMR (DMSO-d₆, δ): 0.92 (3H, t, J=7.2 Hz), 1.29 (3H, d, J=7.2 Hz), Ca. 1.2~1.8 (4H, m), Ca. 2.4~2.8 (2H, m), 2.8~3.1 (2H, m), 4.77 (1H; d,q; J=3.2, 7.2 Hz), 3.8~4.1 (2H, m), 7.25 (1H, d, J=10 Hz), 7.5~7.8 (3H, m), 10.15 (1H, b.s.)

EXAMPLE 69

(1) 7-(2-Hydroxyimino-1-thiosemicarbazonopropyl)-1,3,4,5-tetrahydro-2H-1-benzazepin-2-one (9.81 g) was obtained from 7-(2-hydroxyiminopropionyl)-1,3,4,5-tetrahydro-2H-1-benzazepin-2-one (9.59 g) according to a similar manner to that of Example 32-(1).

IR (Nujol): 3400, 3210, 3140, 1670 cm⁻¹

| NMR | (DMSO-d₆, δ): | 1.96 (s) ⎫ |
|---|---|---|
| | | 2.17 (s) ⎭ (3H), |
| | | Ca. 2.0~2.4 (4H, m), |
| | | Ca. 2.6~2.9 (2H, m), |
| | | 6.86~7.73 (3H, m), 8.08 (1H, b.s.), |
| | | 8.5 (2H, b.s.), |
| | | 10.55 (s) ⎫ |
| | | 9.58 (s) ⎭ (1H), |
| 12.12 (s) ⎫ | | |
| 11.74 (s) ⎭ | (1H) | |

(2) 5-Methyl-3-methylthio-6-(2-oxo-1,3,4,5-tetrahydro-2H-1-benzazepin-7-yl)-1,2,4-triazine (2.06 g) was obtained from the above compound (9.57 g) according to a similar manner to that of Example 32-(2).

IR (Nujol): 3170, 1690 cm⁻¹

NMR (DMSO-d₆, δ): Ca. 2.0~2.36 (4H, m), 2.53 (3H, s), 2.64 (3H, s), Ca. 2.6~2.97 (2H, m), 7.11 (1H, d, J=9 Hz), 7.45~7.69 (2H, m), 9.65 (1H, s)

(3) 5-Methyl-6-(2-oxo-1,3,4,5-tetrahydro-2H-1-benzazepin-7-yl)-4,5-dihydro-1,2,4-triazin-3(2H)-one (1.06 g) was obtained from the above compound (1.95 g) according to a similar manner to that of Example 32-(3). mp > 300° C. (from aqueous acetic acid)

IR (Nujol): 3230, 3100, 1690, 1650 (shoulder) cm⁻¹

NMR (DMSO-d₆, δ): 1.21 (3H, t, J=7 Hz), 2.0~2.38 (4H, m), Ca. 2.5~3.0 (2H, m), 4.62 (1H; d,q; J=3, 7 Hz), 6.98 (1H, d, J=8 Hz), 7.38 (1H, b.s.), 7.56 (1H; d,d; J=2, 8 Hz), 7.63 (1H, d, J=2 Hz), 9.58 (1H, b.s.), 9.92 (1H, b.s.)

Anal. Calcd. for C₁₄H₁₆N₄O₂: C, 61.75; H, 5.92; N, 20.57. Found: C, 61.47; H, 5.77; N, 20.31.

EXAMPLE 70

(1) 6-(4-Chlorophenyl)-3-hydrozino-5-methyl-2,5-dihydro-1,2,4-triazine hydrochloride (5.96 g) was obtained from 3-(2-t-butoxycarbonylhydrazino)-5-methyl-6-(4-chlorophenyl)-2,5-dihydro-1,2,4-triazine (14.1 g) according to a similar manner to that of Example 13-(4). This compound was confirmed to be identical with the object compound of Example 25-(4) by physical data. mp 206°~208° C.

EXAMPLE 71

2,5-Dimethyl-6-(1-methyl-2-oxo-1,2,3,4-tetrahydroquinolin-6-yl)-4,5-dihydro-1,2,4-triazin-3(2H)-one (0.42 g) was obtained from 5-methyl-3-methylthio-6-(1-methyl-2-oxo-1,2,3,4-tetrahydroquinolin-6-yl)-1,2,4-triazine (2.38 g) according to a similar manner to that of Example 28-(1) and 28-(2) except that alkylation was conducted by methyl iodide. mp 196°~198° C. (crystalized from acetone)

NMR (DMSO-d₆, δ): 1.17 (3H, d, J=6.8 Hz), Ca. 2.4~3.1 (4H, m), 3.23 (6H, s), 4.61 (1H; d,q; J=4, 6.8 Hz), 7.02 (1H, d, J=9.2 Hz), 7.3~7.7 (3H, m)

Anal. Calcd. for C₁₅H₁₈N₄O₂: C, 62.92; H, 6.34; N, 19.57. Found: C, 62.99; H, 6.38; N, 19.39.

EXAMPLE 72

3-(2-t-Butoxycarbonylhydrazino)-5-methyl-6-(1-methyl-2-oxo-1,2,3,4-tetrahydroquinolin-6-yl)-2,5-dihydro-1,2,4-triazine (4.72 g) was obtained from 3-(2-t-butoxycarbonylhydrazino)-5-methyl-6-(1-methyl-2-oxo-1,2,3,4-tetrahydroquinolin-6-yl)-1,2,4-triazine (6.77 g) according to a similar manner to that of Example 2-(2). mp 196.5° C. (dec.) (recrystallized from methanol)

NMR (DMSO-d₆, δ): 1.15 (3H, d, J=6.5 Hz), 1.40 (9H, s), 2.37~3.10 (4H, m), 3.24 (3H, s), 4.53 (1H, q, J=6.5 Hz), 7.06 (1H, d, J=9 Hz), 7.4~7.7 (2H, m), 8.2 (2H, b.s.)

Anal. Calcd. for C₁₉H₂₆N₆O₃: C, 59.05; H, 6.78; N, 21.75. Found: C, 58.80; H, 6.63; N, 22.13.

EXAMPLE 73

A mixture of 5-methyl-6-(1-methyl-2-oxo-1,2,3,4-tetrahydroquinolin-6-yl)-4,5-dihydro-1,2,4-triazin-3(2H)-one (81.6 mg), methyl isocyanate (0.5 ml) and triethylamine (1 ml) in methylene chloride (10 ml) was stirred for 18 hours at ambient temperature and evaporated under reduced pressure. The residue was chromatographed on silica gel (5 g) and the eluates with chloroform was evaporated to give 2,4-bis(methylcarbamoyl)-5-methyl-6-(1-methyl-2-oxo-1,2,3,4-tetrahydroquinolin-6-yl)-4,5-dihydro-1,2,4-triazin-3(2H)-one (71 mg).

NMR (DMSO-d₆, δ): 1.31 (3H, d, J=7 Hz), Ca. 2.5 to 3.0 (4H, m), 2.78 (6H, d, J=5 Hz), 3.28 (3H, s), 5.82 (1H, q, J=7 Hz), 7.18 (1H, d, J=8 Hz), 7.7~7.95 (2H, m), 8.16 (1H, q, J=5 Hz), 8.52 (1H, q, J=5 Hz)

EXAMPLE 74

A mixture of 5-methyl-6-(1-methyl-2-oxo-1,2,3,4-tetrahydroquinolin-6-yl)-4,5-dihydro-1,2,4-triazin-3(2H)-one (1.088 g), R-α-methylbenzyl isocyanate (2 ml) and triethylamine (4 ml) in methylene chloride (100 ml) was stirred at room temperature for 87 hours and evaporated under reduced pressure. The residue was dissolved in a small volume of chloroform and purified by column chromatography on silica gel (20 g) with chloroform and then a mixture of chloroform and methanol (50:1 to 10:1) as an eluent to give an oil of a diastereomeric mixture of the object compound (1.16 g).

The separation of the above isomers was conducted by preparative high performance liquid chromatography (Waters Prep-LC500, silica gel column, solvent: 7.5% tetrahydrofuran in methylene chloride, flow late: 150 ml/min., UV detector $\lambda = 254$ nm).

The first fraction was evaporated under reduced pressure and further purified by preparative silica gel thin layer chromatography (solvent; a mixture of chloroform and methanol=50:1) to give (+)-2,4-bis(R-α-methylbenzylcarbamoyl)-5-methyl-6-(1-methyl-2-oxo-1,2,3,4-tetrahydroquinolin-6-yl)-4,5-dihydro-1,2,4-triazin-3(2H)-one (0.231 g).

$[\alpha]_D = +164.9°$ (C 1.0, CHCl$_3$)

NMR (CDCl$_3$, δ) : 1.34 (3H, d, J=7 Hz), 1.52 (3H, d, J=7 Hz), 1.63 (3H, d, J=7 Hz), 2.5∼3.1 (4H, m), 3.36 (3H, s), 4.89∼5.33 (2H, m), 5.98 (1H, q, J=7 Hz), 7.02 (1H, d, J=9 Hz), 7.25∼7.54 (10H, b.s.), 7.6∼7.9 (2H, m), 8.09 (1H, d, J=8 Hz), 9.1 (1H, d, J=8 Hz)

The second fraction gave the (−) isomer, namely, (−)-2,4-bis(R-α-methylbenzylcarbamoyl)-5-methyl-6-(1-methyl-2-oxo-1,2,3,4-tetrahydroquinolin-6-yl)-4,5-dihydro-1,2,4-triazin-3(2H)-one (0.188 g) by treating with a same manner as above.

$[\alpha]_D = -110.1°$ (C 1.0, CHCl$_3$)

NMR (CDCl$_3$, δ) : 1.39 (3H, d, J=7 Hz), 1.57 (3H, d, J=7 Hz), 1.64 (3H, d, J=7 Hz), Ca. 2.5∼3.1 (4H, m), 3.36 (3H, s), 4.89∼5.35 (2H, m), 5.89 (1H, q, J=7 Hz), 6.97 (1H, d, J=9 Hz), 7.23∼7.53 (10H, m), 7.54∼7.83 (2H, m), 8.07 (1H, d, J=7 Hz), 9.07 (1H, d, J=7 Hz)

IR (Nacl, film): 3300, 1735 (shoulder), 1725, 1705, 1670

EXAMPLE 75

(−)-2,4-Bis(R-α-methylbenzylcarbamoyl)-5-methyl-6- (1-methyl-2-oxo-1,2,3,4-tetrahydroquinolin-6-yl)-4,5-dihydro-1,2,4-triazin-3(2H)-one (168 mg) was heated at 220° C. for 20 minutes under argon atmosphere. After cooling, the resultant product was dissolved in chloroform and chromatographed on silica gel (5 g). The eluates with a mixture of chloroform and methanol (50:1 to 20:1) were evaporated and the residue was triturated with diethyl ether to give crystals of (−)-5-methyl-6-(1-methyl-2-oxo-1,2,3,4-tetrahydroquinolin-6-yl)-4,5-dihydro-1,2,4-triazin-3(2H)-one (66 mg).

Mass.: m/e 272 (M$^+$)

$[\alpha]_D = -280.3°$ (C 1.0, CH$_3$OH)

NMR (CD$_3$OD, δ): 1.34 (3H, d, J=7 Hz), 2.46∼3.23 (4H, m), 4.73 (1H, q, J=7 Hz), 4.75 (3H, s), 7.15 (1H, d, J=9 Hz), 7.56∼7.79 (2H, m)

EXAMPLE 76

(+)-5-Methyl-6-(1-methyl-2-oxo-1,2,3,4-tetrahydroquinolin-6-yl)-4,5-dihydro-1,2,4-triazin-3(2H)-one (81 mg) was obtained from (+)-2,4-bis(R-α-methylbenzylcarbamoyl)-5-methyl-6-(1-methyl-2-oxo-1,2,3,4-tetrahydroquinolin-6-yl)-4,5-dihydro-1,2,4-triazin-3(2H)-one (211 mg) according to a similar manner to that of Example 75.

mass.: m/e 272 (M$^+$)

$[\alpha]_D = +283.6°$ (C 1.0, CH$_3$OH)

NMR (CH$_3$OD, δ) : 1.33 (3H, d, J=7 Hz), 2.45∼3.16 (4H, m), 4.72 (1H, q, J=7 Hz), 4.75 (3H, s), 7.13 (1H, d, J=9 Hz), 7.53∼7.78 (2H, m)

EXAMPLE 77

(1) 3-Carboxymethylthio-5-methyl-6-(1-methyl-2-oxo-1,2,3,4-tetrahydroquinolin-6-yl)-1,2,4-triazine (4.76 g) was obtained by reacting 6-(2-hydroxyimino-1-thiosemicarbazonopropyl)-1-methyl-2-oxo-1,2,3,4-tetrahydroquinoline (5.65 g) with potassium carbonate and then reacting with sodium chloroacetate (3.09 g) instead of methyl iodide according to a similar manner to that of Example 32-(2).

IR (Nujol) : 3050 (broad), 1740, 1645 cm$^{-1}$

NMR (DMSO-d$_6$, δ): 2.53 (3H, s), Ca. 2.5∼2.79 (2H, m), 2.83∼3.1 (2H, m), 3.31 (3H, s), 4.11 (2H, s), 7.26 (1H, d, J=8 Hz), 7.59 (1H, d, J=2 Hz), 7.64 (1H; d,d; J=2, 8 Hz)

(2) 5-Methyl-6-(1-methyl-2-oxo-1,2,3,4-tetrahydroquinolin-6-yl)-4,5-dihydro-1,2,4-triazin-3(2H)-one (0.31 g) was obtained by treating the above compound (0.7 g) with potassium hydroxide and then sodium borohydride according to a similar manner to that of Example 32-(3). This compound was confirmed identical with the object compound of Example 49-(3) by the physical data. mp 242°∼243° C.

NMR (DMSO-d$_6$, δ): 1.43 (3H, d, J=6 Hz), 2.4∼3.1 (4H, m), 3.23 (3H, s), 4.63 (1H; d, q; J=3 Hz, 6 Hz), 7.06 (1H, d, J=9.5 Hz)

EXAMPLE 78

(1) 7-(2-Hydroxyimino-1-thiosemicarbazonopropyl)-1-methyl-1,3,4,5-tetrahydro-2H-1-benzazepin-2-one (9.37 g) was obtained from 7-(2-hydroxyiminopropionyl)-1-methyl-1,3,4,5-tetrahydro-2H-1-benzazepin-2-one (7.42 g) in a similar manner to that of Example 32-(1).

IR (Nujol): 3350, 3220, 3150, 1650, 1600 cm$^{-1}$

| NMR (DMSO-d$_6$, δ): | 1.9∼2.4 (4H, m), 2.17 (3H, s), Ca: 2.5∼2.9 (2H, m), 3.25 (3H, s), 7.1∼7.7 (3H, m), 8.08 (b.s.) ⎫ 8.83 (b.s.) ⎭ (1H) 8.61 (b.s.) ⎫ 11.71 (s) ⎫ 10.66 (b.s.) ⎭ (2H), 12.11 (s) ⎭ (1H) |
|---|---|

(2) A mixture of the above obtained compound (9.18 g), sodium bicarbonate (13.86 g), water (100 ml) and methanol (100 ml) was refluxed for 5 hours with stirring and filtered by suction. To the filtrate was added methyl iodide (3.9 g) under stirring and the mixture was stirred for 30 minutes at room temperature. The solution was evaporated under reduced pressure and the residue was extracted with chloroform after addition of water. The extract was chromatographed on silica gel (100 g) using chloroform as an eluent. The eluates were evaporated and the residue was triturated with diethyl ether to give crystals of 5-methyl-6-(1-methyl-2-oxo-1,3,4,5-tetrahydro-2H-1-benzazepin-7-yl)-3-methylthio-1,2,4-triazine (4.89 g).

NMR (CDCl$_3$, δ): 2.0∼2.4 (4H, m), 2.60 (3H, s), 2.70 (3H, s), Ca. 2.6∼3.0 (2H, m), 3.40 (3H, s), 7.2∼7.7 (3H, m)

(3) 5-Methyl-6-(1-methyl-2-oxo-1,3,4,5-tetrahydro-2H-1-benzazepin-7yl)-4,5-dihydro-1,2,4-triazin-3(2H)-one (1.56 g) was obtained from the compound (3.0 g) obtained in the above 1 in a similar manner to that of Example 32-(3). mp 162° to 168° C. (recrystallized from ethanol)

IR (Nujol): 3550 (shoulder), 3460, 3200, 3070, 1695, 1640, 1620 cm$^{-1}$

NMR (DMSO-d$_6$, δ): 1.22 (3H, d, J=7 Hz), 1.9~2.4 (4H, b.m), 2.5~2.9 (2H, b.m.), 4.68 (1H; d, q; J=3, 7 Hz), 7.33 (1H, d, J=8.8 Hz), Ca. 7.4 (1H, b.s.), 7.6~7.9 (2H, m), 10.02 (1H, d, J=2 Hz)

EXAMPLE 79

(1) 1-Butyl-7-(2-hydroxyimino-1-thiosemicarbazonopropyl)-1,3,4,5-tetrahydro-2H-1-benzazepin-2-one (6.81 g) was obtained from 1-n-butyl-7-(2-hydroxyiminopropionyl)-1,3,4,5-tetrahydro-2H-1-benzazepin-2-one (7.5 g) in a similar manner to that of Example 32-(1)

IR (Nujol): 3250, 3160, 1645, 1615, 1600 cm$^{-1}$

NMR (DMSO-d$_6$, δ): 0.83 (3H, t, J = 6Hz), Ca. 1.0~1.7 (4H, m), 1.9~2.4 (4H, m), 2.17 (3H, s), Ca. 2.5~3.0 (2H, m), 3.6~4.1 (2H, m), 7.1~7.8 (3H, m), 8.13 ⎫ 8.69 ⎭ (1H, b.s.) 8.56 ⎫ 10.66 ⎭ (2H, b.s.), 11.69 ⎫ 12.08 ⎭ (1H, s)

(2) 6-(1-Butyl-2-oxo-1,3,4,5-tetrahydro-2H-1-benzazepin-7-yl)-5-methyl-3-methylthio-1,2,4-triazine (4.96 g) was obtained from the above compound (6.7 g) in a similar manner to that of Example 78-(2).

IR (film): 1660, 1605 cm$^{-1}$

NMR (CDCL$_3$, δ): 0.89 (3H, t, J=6 Hz), 1.1~1.8 (4H, m), 2.1~2.5 (4H, m), 2.59 (3H, s), 2.69 (3H, s), Ca. 2.6~3.0 (2H, m), 3.7~4.1 (2H, m), 7.2~7.7 (3H, m)

(3) Crude oil of 6-(1-butyl-2-oxo-1,3,4,5-tetrahydro-2H-1-benzazepin-7-yl)-5-methyl-4,5-dihydro-1,2,4-triazin-3(2H)-one was obtained from the above compound (4.78 g) in a similar manner to that of Example 32-(3). The purification was conducted by column chromatography on silica gel (20 g) with a mixture of chloroform and ethyl acetate (10:1) as an eluent to give pure compound (1.62 g).

NMR (DMSO-d$_6$, δ): 0.81 (3H, t, J=5.6 Hz), Ca. 1.0~1.7 (4H, m), 1.25 (3H, d, J=6 Hz), 1.8~2.4 (4H, b.m), Ca. 2.5~3.0 (2H, b.m), 3.6~4.1 (2H, m), 4.67 (1H; d,q; J=3.2, 6 Hz), 7.35 (1H, d, J=10 Hz), Ca. 7.4 (1H, b.s), 7.5~7.9 (2H, m), 10.03 (1H, b.s)

EXAMPLE 80

(1) A mixture of 5-methyl-3-methylthio-6-phenyl-1,2,4-triazine (2.17 g) and 3-[3(1-pyrrolidinylmethyl)-phenoxy]propylamine (3.04 g) was heated at 150° C. for 33 hours and dissolved in a small volume of chloroform after cooling. The solution was purified by column chromatgraphy on silica gel (100 g) with chloroform and then a mixture of chloroform and methanol (20:1) as eluents to give 3-[3-[3-(1-pyrrolidinylmethyl)-phenoxy]-propylamino]-5-methyl-6-phenyl-1,2,4-triazine (2.57 g).

IR (film): 3230, 3050, 2920, 2770 cm$^{-1}$

NMR (CDCL$_3$, δ): 1.77 (4H, m), 2.16 (2H; t,t; J=6, 6 Hz), 2.39 (3H, s), 2.52 (4H, m), 3.60 (2H, s), 3.77 (2H; d, t; J=6, 6 Hz), 4.12 (2H, t, J=6 Hz), 5.80 (1H, m), 6.9 (3H, m), 7.2 (1H, m), 7.46 (5H, m)

(2) To a solution of the above compound (2.57 g) and sodium cyanoborohydride (0.8 g) in a methanol (50 ml) was dropwise added 10% methanolic solution of hydrogen chloride (20 ml) over a period of 40 minutes under stirring. Then the mixture was stirred for 30 minutes. To the reaction mixture was added sodium bicarbonate (4.5 g), and the mixture was stirred for 30 minutes, treated with activated charcoal, and filtered by suction. The filtrate was evaporated and the residue was chromatographed on silica gel (70 g) using chloroform and then a mixture of chloroform and methanol (50:1 to 100:7) as eluents. The eluates with a mixture of chloroform and methanol (100:7) were evaporated under reduced pressure to give an oil of 3-[3-[3-(1-pyrrolidinylmethyl)-phenoxy]propylamino]-5-methyl-6-phenyl-2,5-dihydro-1,2,4-triazine (1.47 g).

IR (film): 3300 (broad), 2950, 1670, 1600, 1450, 1340, 1260, 1175, 1050 cm$^{-1}$ NMR (CDCL$_3$, δ): 1.35 (3H, d, J=6 Hz), 2.10 (6H, m), 3.31 (4H, m), 3.72 (2H, m), 4.21 (2H, m), 4.33 (2H, s), 4.90 (1H, m), 6.9~7.8 (9H, m)

EXAMPLE 81

(1) 2-Hydroxyimino-3'-methylpropiophenone thiosemicarbazone (24.2 g) was obtained from 2-hydroxyimino-3'-methylpropiophenone (17.7 g) in a similar manner to that of Example 32-(1). mp 210° to 215° C. (dec.) (recrystallized from methanol)

IR (Nujol): 3400, 3330, 3230, 1610 cm$^{-1}$

NMR (DMSO-d$_6$, δ): 2.12 (3H, s), 2.30 (3H, s), 7.0 (2H, m), 7.3 (2H, m), 8.08 (1H, b.s.), 8.30 (1H, s), 8.57 (1H, b.s.), 11.68 (1H, s)

(2) 5-Methyl-3-methylthio-6-(m-tolyl)-1,2,4-triazine (4.2 g) was obtained as an oil from the above compound (10 g) in a similar manner to that of Example 32-(2).

IR (film/NaCl): 2900, 1675, 1600, 1585, 1490, 1420, 1350 cm$^{-1}$

NMR (CDCl$_3$, δ): 2.34 (3H, s), 2.51 (3H, s), 2.68 (3H, s), 7.34 (4H, m)

(3) 5-Methyl-6-(m-tolyl)-4,5-dihydro-1,2,4-triazin-3(2H)-one (0.92 g) was obtained from the above compound (4 g) in a similar manner to that of Example 32-(3). mp 201° to 204° C. (recrystallized from a mixture of dimethylformamide and ethanol).

IR (Nujol): 3200, 3070, 1700, 1670 cm$^{-1}$

NMR (DMSO-d$_6$, δ): 1.26 (3H, d, J=7 Hz), 2.39 (3H, s), 4.73 (1H, m), 7.3~7.7 (5H, m), 10.15 (1H, s)

Anal. Calcd. for C$_{11}$H$_{13}$N$_3$O: C, 65.00; H, 6.45; N, 20.68. Found: C, 64.64; H, 6.31; N, 20.56.

EXAMPLE 82

(1) A mixture of 2-hydroxyimino-3'-methylpropiophenone thiosemicarbazone (5 g) and potassium carbonate (6.1 g) in water (44 ml) was refluxed for 4 hours under nitrogen atmosphere. The reaction mixture was treated with activated charcoal and filtered by suction. The filtrate was acidified with diluted hydrochloric acid, and the resultant precipitates were collected by filtration, washed with water and dried. The above obtained crude product was dissolved in methanol (150 ml), and the solution was filtered by suction. The filtrate was concentrated under reduced pressure, and the residue was crystallized from diisopropyl ether, collected by filtration, washed with a mixture of methanol and diisopropyl ether, and dried to give 5-methyl-6-(m-tolyl)-1,2,4-triazine-3(2H)-thione (5 g).

IR (Nujol): 3170, 1670, 1620 cm$^{-1}$ (2) 5-Methyl-6-(m-tolyl)-4,5-dihydro-1,2,4-triazine-3(2H)-thione (1.12 g) was obtained from the above compound (3.42 g) by reducing with sodium borohydride (1.16 g) in a mixture of methanol (17 ml) and tetrahydrofuran (17 ml) according to a similar manner to that of Example 35-(3). mp 186° to 191° C. (recrystallized from ethanol).

IR (Nujol): 3180, 1570 cm$^{-1}$

NMR (DMSO-d$_6$, δ): 1.22 (3H, d, J=7 Hz), 2.35 (3H, s), 4.66 (1H, m), 7.50 (2H, m), 7.60 (2H, m), 9.23 (1H, m), 11.38 (1H, s)

Anal. Calcd. for C$_{11}$H$_{13}$N$_3$S: C, 60.24; H, 5.97; N, 19.16; S. 14.62. Found: C, 59.87; H, 5.98; N, 18.87; S, 14.25.

What is claimed is:

1. A compound of the formula:

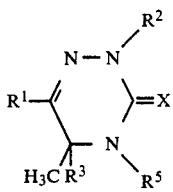

wherein R$^1$ pyridyl, thienyl, 2-oxo-1,2,3,4,-tetrahydroquinolyl or 2-oxo-1,3,4,5-tetrahydro-2H-1-benazepinyl optionally substituted with lower alkyl, lower alkoxy, halogen, or nitro;
  R$^2$ is hydrogen, lower alkyl or carbamoyl substituted with lower alkyl or ar(lower)alkyl wherein ar is phenyl, xylyl, tolyl or naphthyl;
  R$^3$ is hydrogen or ar(lower)alkyl wherein ar is phenyl, tolyl, xylyl or naphthyl;
  R$^5$ is hydrogen, lower alkyl or carbamoyl substituted with lower alkyl or ar(lower)alkyl wherein ar is phenyl, tolyl, xylyl or naphthyl; and
  X is O or S, and pharmaceutically acceptable salt thereof.

2. A compound of claim 1, wherein
  R$^1$ is pyridyl optionally substituted with lower alkyl, lower alkoxy, halogen or nitro;
  R$^2$, R$^3$ and R$^5$ are each hydrogen; and
  X is oxo.

3. A compound of claim 1, wherein
  R$^1$ is thienyl optionally substituted with lower alkyl, lower alkyl alkoxy, halogen or nitro;
  R$^2$, R$^3$ and R$^5$ are each hydrogen; and
  X is oxo.

4. A compound of claim 1, wherein
  R$^1$ is 2-oxo-1,2,3,4-tetrahydroquinolyl optionally substituted with lower alkyl, lower alkoxy, halogen, or nitro.

5. A compound of claim 4, wherein
  R$^1$ is 2-oxo-1,2,3,4-tetrahydroquinolyl optionally substituted with lower alkyl.

6. A compound of claim 5, wherein
  R$^3$ is hydrogen; and
  X is oxo.

7. A compound of claim 6, wherein
  R$^1$ is 2-oxo-1,2,3,4-tetrahydroquinolyl substituted with lower alkyl.

8. A compound of claim 7, which is 5-methyl-6-(1-methyl-2-oxo-1,2,3,4-tetrahydroquinolin-6-yl)-4,5-dihydro-1,2,4-triazin-3(2H)-one.

9. A compound of claim 8, which is (−) isomer.

10. A compound of claim 8, which is (+) isomer.

11. A compound of claim 7, which is 5-methyl-6-(1-butyl-2-oxo-1,2,3,4-tetrahydroquinolin-6-yl)-4,5-dihydro-1,2,4-triazin-3(2H)-one.

12. A compound of claim 6, wherein
  R$^1$ is unsubstituted 2-oxo-1,2,3,4-tetrahydroquinolyl.

13. A compound of claim 1, wherein
  R$^1$ is 2-oxo-1,3,4,5-tetrahydro-2H-1-benzazepinyl optionally substituted with lower alkyl, lower alkoxy, halogen, or nitro.

14. A compound of claim 13, wherein
  R$^1$ is 2-oxo-1,3,4,5-tetrahydro-2H-1-benzazepinyl substituted lower alkyl.

15. A compound of claim 13, wherein
  R$^1$ is unsubstituted 2-oxo-1,3,4,5-tetrahydro-2H-1-benzazepinyl.

16. An antihypertensive pharmaceutical composition comprising an antihypertensively effective amount of a compound of claim 1 or pharmaceutically acceptable salt thereof in association with a pharmaceutically acceptable, substantially non-toxic carrier or excipient.

17. A method for treating hypertension or thrombosis which comprises orally or introperitonealy administering a compound of claim 1 or pharmaceutically acceptable salt thereof to human being or animals.

18. An antithrombotic pharmaceutical composition comprising an antithrombotically effective amount of a compound of claim 1 or pharmaceutically acceptable salt thereof in association with a pharmaceutically acceptable, substantially non-toxic carrier or excipient.

* * * * *